US011286480B2

(12) United States Patent
Beisel et al.

(10) Patent No.: US 11,286,480 B2
(45) Date of Patent: Mar. 29, 2022

(54) METHODS AND COMPOSITIONS FOR SEQUENCE SPECIFIC ANTIMICROBIALS

(71) Applicant: NORTH CAROLINA STATE UNIVERSITY, Raleigh, NC (US)

(72) Inventors: Chase Beisel, Raleigh, NC (US); Ahmed M. Gomaa, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 188 days.

(21) Appl. No.: 15/762,730

(22) PCT Filed: Sep. 27, 2016

(86) PCT No.: PCT/US2016/053892
§ 371 (c)(1),
(2) Date: Mar. 23, 2018

(87) PCT Pub. No.: WO2017/058751
PCT Pub. Date: Apr. 6, 2017

(65) Prior Publication Data
US 2018/0273937 A1 Sep. 27, 2018

Related U.S. Application Data

(60) Provisional application No. 62/233,762, filed on Sep. 28, 2015.

(51) Int. Cl.
| C12N 15/11 | (2006.01) |
| C12N 9/22 | (2006.01) |
| C12N 15/113 | (2010.01) |
| A61K 31/7105 | (2006.01) |

(52) U.S. Cl.
CPC .......... *C12N 15/11* (2013.01); *A61K 31/7105* (2013.01); *C12N 15/113* (2013.01); *C12N 2310/20* (2017.05); *C12N 2310/3513* (2013.01)

(58) Field of Classification Search
None
See application file for complete search history.

(56) References Cited

U.S. PATENT DOCUMENTS

| 9,023,649 | B2 | 5/2015 | Mali et al. |
| 9,260,723 | B2 | 2/2016 | Mali et al. |
| 10,136,649 | B2 * | 11/2018 | Barrangou ............. A01N 37/46 |
| 2006/0199190 | A1 | 9/2006 | Russell et al. |
| 2009/0007301 | A1 | 1/2009 | Wintz et al. |
| 2013/0288251 | A1 | 10/2013 | Horvath et al. |
| 2014/0068797 | A1 | 3/2014 | Doudna et al. |
| 2014/0113376 | A1 | 4/2014 | Sorek et al. |
| 2014/0186958 | A1 | 7/2014 | Zhang et al. |
| 2014/0273233 | A1 | 9/2014 | Chen et al. |
| 2014/0356867 | A1 | 12/2014 | Peter et al. |
| 2014/0356956 | A1 | 12/2014 | Church et al. |
| 2015/0050699 | A1 | 2/2015 | Siksnys et al. |
| 2015/0056628 | A1 | 2/2015 | Russell et al. |
| 2015/0064138 | A1 | 3/2015 | Lu et al. |
| 2015/0093473 | A1 | 4/2015 | Barrangou et al. |
| 2015/0098954 | A1 | 4/2015 | Hyde et al. |
| 2015/0132263 | A1 | 5/2015 | Liu et al. |
| 2015/0291961 | A1 | 10/2015 | Siksnys et al. |
| 2015/0315576 | A1 | 11/2015 | Caliando et al. |
| 2015/0353901 | A1 | 12/2015 | Liu et al. |
| 2016/0017366 | A1 | 1/2016 | Chen et al. |
| 2016/0024510 | A1 | 1/2016 | Bikard et al. |
| 2016/0186152 | A1 | 6/2016 | Brouns et al. |
| 2016/0186213 | A1 | 6/2016 | Zhang et al. |
| 2016/0289700 | A1 | 10/2016 | Barrangou et al. |
| 2016/0298096 | A1 | 10/2016 | Charpentier et al. |
| 2016/0333348 | A1 | 11/2016 | Clube et al. |
| 2016/0345578 | A1 | 12/2016 | Barrangou et al. |
| 2017/0002339 | A1 | 1/2017 | Barrangou et al. |
| 2017/0028083 | A1 | 2/2017 | Beisel et al. |
| 2017/0196225 | A1 | 7/2017 | Clube et al. |
| 2017/0246221 | A1 | 8/2017 | Clube et al. |
| 2017/0275648 | A1 | 9/2017 | Barrangou et al. |
| 2018/0064114 | A1 | 3/2018 | Clube |
| 2018/0064115 | A1 | 3/2018 | Clube et al. |
| 2018/0070594 | A1 | 3/2018 | Clube et al. |
| 2018/0084785 | A1 | 3/2018 | Clube |
| 2018/0084786 | A1 | 3/2018 | Clube |
| 2018/0146681 | A1 | 5/2018 | Clube |
| 2018/0155729 | A1 | 6/2018 | Beisel et al. |
| 2018/0200387 | A1 | 7/2018 | Porteus |
| 2018/0258411 | A1 * | 9/2018 | Kadiyala ............... C12N 15/111 |

FOREIGN PATENT DOCUMENTS

| EP | 2860267 | 4/2015 |
| WO | 2006/113709 | 10/2006 |
| WO | 2010/054154 | 1/2010 |
| WO | 2010/075424 | 7/2010 |
| WO | 2013/098244 | 7/2013 |

(Continued)

OTHER PUBLICATIONS

Boudry et al., Function of the CRISPR-Cas System of the Human Pathogen Clostridium difficile; mBio, vol. 6, No. 5, e011112-15, pp. 1-15, plus 1 page erratum, 2015 (Year: 2015).*

Office Action, U.S. Appl. No. 15/032,985, dated Feb. 5, 2019, 11 pages.

Rath D et al. The CRISPR-Cas immune system: Biology, mechanisms and applications. Biochimie. 2015;117:119-128.

Spath K et al. Lactobacillus plantarum and Lactobacillus buchneri as expression systems: Evaluation of different origins of replication for the design of suitable shuttle vectors. Mol. Biotechnol. 2012; 52: 40-48.

Grissa I et al. The CRISPRdb database and tools to display CRISPRs and to generate dictionaries of spacers and repeats. BMC Bioinformatics. 2007; 8(172): pp. 1-10.

Beisel CL et al. A CRISPR design for next-generation antimicrobials. Genome Biology. 2014; 15: 516, 4 pages.

(Continued)

*Primary Examiner* — Channing S Mahatan
(74) *Attorney, Agent, or Firm* — Myers Bigel, P.A.

(57) ABSTRACT

The invention relates to antimicrobial compositions comprising cell-penetrating peptides linked to CRISPR RNAs and methods for their use.

8 Claims, 5 Drawing Sheets

Specification includes a Sequence Listing.

(56) References Cited

FOREIGN PATENT DOCUMENTS

| | | |
|---|---|---|
| WO | 2013/141680 | 9/2013 |
| WO | WO 2013/176772 | 11/2013 |
| WO | 2013/188522 | 12/2013 |
| WO | 2013/188638 | 12/2013 |
| WO | 2014/022702 | 2/2014 |
| WO | 2014/065596 | 5/2014 |
| WO | 2014/071235 | 5/2014 |
| WO | 2014/093479 | 6/2014 |
| WO | 2014/110006 | 7/2014 |
| WO | 2014/113493 | 7/2014 |
| WO | 2014/124226 | 8/2014 |
| WO | 2014/144155 | 9/2014 |
| WO | 2014/144592 | 9/2014 |
| WO | 2014/150624 | 9/2014 |
| WO | 2014/186686 | 11/2014 |
| WO | 2014/191128 | 12/2014 |
| WO | 2014/191518 | 12/2014 |
| WO | 2014/201015 | 12/2014 |
| WO | 2014/204727 | 12/2014 |
| WO | 2015/021353 | 2/2015 |
| WO | 2015/026886 | 2/2015 |
| WO | 2015/034872 | 3/2015 |
| WO | 2015/035139 | 3/2015 |
| WO | 2015/040402 | 3/2015 |
| WO | 2015/053995 | 4/2015 |
| WO | 2015/070193 | 5/2015 |
| WO | 2015/077290 | 5/2015 |
| WO | 2015/089277 | 6/2015 |
| WO | 2015/089406 | 6/2015 |
| WO | WO 2015/089486 | 6/2015 |
| WO | 2015112896 A2 | 7/2015 |
| WO | 2015/116686 | 8/2015 |
| WO | 2015/119941 | 8/2015 |
| WO | 2015/139139 | 9/2015 |
| WO | 2015/148680 | 10/2015 |
| WO | 2015/153791 | 10/2015 |
| WO | 2015/153889 | 10/2015 |
| WO | 2015/153940 | 10/2015 |
| WO | 2015/155686 | 10/2015 |
| WO | 2015/159068 | 10/2015 |
| WO | 2015/159086 | 10/2015 |
| WO | 2015/159087 | 10/2015 |
| WO | 2015/160683 | 10/2015 |
| WO | 2015/189693 | 12/2015 |
| WO | 2015/200555 | 12/2015 |
| WO | 2016/084088 | 6/2016 |
| WO | 2016/177682 | 11/2016 |
| WO | 2016/196361 | 12/2016 |
| WO | 2017/027423 | 2/2017 |
| WO | 2017/066497 | 4/2017 |
| WO | 2017/112620 | 6/2017 |
| WO | 2017/0147507 | 8/2017 |

OTHER PUBLICATIONS

Citorik RJ et al. "Sequence-specific antimicrobials using efficiently delivered RNA-guiding nucleases Supplemental Material." Nature Biotechnology. Sep. 21, 2014; 32(11): 1141-1145. DOI:10.1038/nbt.3011, 14 pages.

Final Office Action, U.S. Appl. No. 15/113,656, dated Jul. 30, 2018, 8 pages.

Liu S et al. Complete genome sequence of Lactobacillus buchneri NRRL B-30929, a novel strain from a commercial ethanol plant. Journal of Bacteriology. Aug. 2011; 193(15): 4019-4020.

Liu S et al. NCBI (2011) CRISPR-associated protein, Csn1 family [Lactobacillus buchneri], pp. 1-3.

International Search Report and Written Opinion, PCT/US2018/034322, dated Sep. 13, 2018, 7 pages.

Ajdic et al. "hypothetical protein SMU_1405c [*Streptococcus mutans* UA159]", Proc. Natl. Acad. Sci. U.S.A. 99 (22), 14434-14439 (2002) URL: https://www.ncbi.nlm.nih.gov/protein/NP_721764.1/, retrieved Jul. 20, 2018.

Barrangou R. "CRISPR-Cas systems and RNA-guided interference", Wiley interdisciplinary reviews, RNA (2013) 4: pp. 267-278.

Barrangou R., et al. "CRISPR-Cas systems: prokaryotes upgrade to adaptive immunity", Mol Cell (2014) 54(2): pp. 234-244.

Barrangou R., et al. "CRISPR: new horizons in phage resistance and strain identification" Annu Rev Food Sci Technol (2012) 3, pp. 143-162.

Barrangou, R, "Diversity of CRISPR-Cas immune systems and molecular machines", Genome Biology (2015) 16:247, 11 pages.

Barrangou, R., et al. "CRISPR provides acquired resistance against viruses in prokaryotes", Science (2007) 315(5819): pp. 1709-1712.

Bhaya et al. "CRISPR-Cas Systems in Bacteria and Archaea: Versatile Small RNAs for Adaptive Defense and Regulation", Annu. Rev. Genet. (2011) 45: pp. 273-297.

Bikard D. et al. "Programmable repression and activation of bacterial gene expression using an engineered CRISPR-Cas system" Nucleic Acids Res (2013) 41(15): pp. 7429-7437.

Bikard D., et al. "CRISPR interference can prevent natural transformation and virulence acquisition during in vivo bacterial infection". Cell Host & Microbe (2012), 10 pages.

Bikard D., et al. "Exploiting CRISPR-Cas nucleases to produce sequence-specific antimicrobial", Nature Biotechnology 2014, 6 pages.

Briner AE, Barrangou R, "Lactobacillus buchneri Genotyping on the Basis of Clustered Regularly Interspaced Short Palindromic Repeat (CRISPR) Locus Diversity", Appl Environ Microbiol. 80:994-1001. (2014).

Briner et al. "Guide RNA Functional Modules Direct Cas9 Activity and Orthogonality", Molecular Cell (2014) 56(2): pp. 333-339.

Brouns SJJ, et al., "Small CRISPR RNAs guide antiviral defense in prokaryotes", Science (2008) 321:5891, pp. 960-964.

Carte et al. "The three major types of CRISPR-Cas systems function independently in CRISPR RNA biogenesis in *Streptococcus thermophilus*". Molecular Microbiology, 93(1). pp. 98-112 (2014).

Chylinski et al. "Classification and evolution of type II CRISPR-Cas Systems", Nucleic Acids Research, (2014) 15 pages.

Chylinski Krzysztof et al., "The tracrRNA and Cas9 families of type II CRISPR-Cas immunity systems", RNA biology, 10:5, 13 pages (2013).

Citorik R. et al., "Sequence-specific antimicrobials using efficiently delivered RNA-guided nucleases", Nature Biotechnology 2014, 7 pages.

Cochrane Kyla et al., "Complete genome sequences and analysis of the Fusobacterium nucleatum subspecies animalis 7-1 bacteriophage PHIFunu1 and PHIFunu2", Anaerobe, 38:125-129 (2016).

Cong et al. "Multiplex Genome Engineering Using CRISPR/Cas Systems" Science (2013) vol. 339 (6121): pp. 819-823.

Darmon E. Leach DF "Bacterial Genome Instability", Microbiol. Mol. Biol. Rev. (2014) vol. 78. pp. 1-39.

Deltcheva, E. et al. "CRISPR RNA maturation by trans-encoded small RNA and host factor RNase III", Nature, vol. 471, (Mar. 2011) pp. 602-607.

Doench et al. "Rational design of highly active sgRNAs for CRISPR-Cas9-mediated gene inactivation", Nature Biotechnology, 32:12 (2014) 8 pages.

Dupuis ME et al., "CRISPR-Cas and restriction-modification systems are compatible and increase phage resistance", Nat Commun., vol. 4, p. 2087 (2013).

Edgar R., et al. "The *Escherichia coli* CRISPR System Protects from Lysogenization, Lysogens, and Prophage Induction", Journal of Bacteriology (2010), vol. 132, No. 23, pp. 6292-6294.

Estvelt et al. "Orthogonal Cas9 proteins for RNA-guided gene regulation and editing". Nature Methods, 10:11 (2013) pp. 1116-1121.

Fonfara, I. et al. "Phytogeny of Cas9 determines functional exchangeability of dual-RNA and Cas9 among orthologous type II CRISPR-Cas systems", Nucleic Acids Res (2013) 14 pages.

Fu et al. "Improving CRISPR-Cas nuclease specificity using truncated guide RNAs", Nature Biotechnology, 32:3 (2013) 9 pages.

Garneau JE. et al. "The CRISPR/Cas bacterial Immune system cleaves bacteriophage and plasmid DNA" Nature (2010) 468(7320): pp. 67-71.

(56) References Cited

OTHER PUBLICATIONS

Gasiunas et al. "Cas9-crRNA ribonucleoprotein complex mediates specific DNA cleavage for adaptive immunity in bacteria", Proc. Natl. Acad. Sci. (2012), 109:E2579-E2586.
Gilbert et al. "Genome-Scale CRISPR-Mediated Control of Gene Repression and Activation", Cell, 159 (2014) pp. 647-661.
Gilbert, L. A. et al. "CRISPR-Mediated Modular RNA-Guided Regulation of Transcription in Eukaryotes", Cell 154, (2013) pp. 442-451.
Gomaa AA, et al. "Programmable Removal of Bacterial Strains by Use of Genome-Targeting CRISPR-Cas Systems", mBic(2014). 6(1):e00928-13.
Haurwitz et al. "Sequence- and Structure-Specific RNA Processing by a CRISPR Endonuclease". Science (2010) 329: pp. 1355-1358.
Heinl, Stefan et al. "Insights into the completely annotated genome of Lactobacillus buchneri CD034, a strain isolated from stable grass silage", Journal of Biotechnology, 161:153-166 (2012).
Horvath and Barrangou "CRISPR/Cas, the Immune System of Bacteria and Archaea", Science (2010) 327, pp. 167-170.
Horvath, P. et al. "Diversity, Activity, and Evolution of CRISPR Loci in *Streptococcus thermophilus*", J Bacteriol. 190 (2008) pp. 1401-1412.
Hsu et al. "DNA targeting specificity of RNA-guided Cas9 nucleases", Nature Biotechnology, 31:9 (2013) pp. 827-834.
International Search Report and Written Opinion for PCT/US2015/047136 dated Nov. 26, 2015, 10 pages.
Jiang, W. et al. "Dealing with the Evolutionary Downside of CRISPR Immunity: Bacteria and Beneficial Plasmids", PLOS Genetics (2013) vol. 9, issue 9, 13 pages.
Jiang, W. et al. "RNA-guided editing of bacterial genomes using CRISPR-Cas systems", Nat. Biotechnol. (2013) vol. 31, pp. 233-239.
Jinek et al. "A Programmable Dual-RNA-Guided DNA Endonuclease in Adaptive Bacterial Immunity", Science (2012) vol. 337, pp. 816-821.
Jinek. M. et al.,"Structures of Cas9 endonucleases reveal RNA-mediated conformational activation", Science (2014) vol. 343, 6176, 28 pages.
Karvelis et al. "crRNA and tracrRNA guide Cas9-mediated DNA interference in *Streptococcus thermophilus*", RNA Biol. (2013) vol. 10: pp. 841-851.
Karvelis, Tautvydas et al., "crRNA and tracerRNK guide Cas9-mediated DNA interference in *Streptococcus thermophilus*," RNA Biology, 2013, vol. 10, Issue 5, pp. 841-851.
Karvelis, Tautvydas et al., "Programmable DNA cleavage in vitro by Cas9," Biochem. Soc. Trans. 2013, vol. 41, part 6, pp. 1401-1406.
Kobayashi K, et al. "Essential Bacillus subtilis genes". Proc. Natl. Acad. Sci. U.S.A. (2003) vol. 100, pp. 4678-4683.
Labrie SJ et al. "Bacteriophage resistance mechanisms" Nat. Rev. Microbiol (2010) vol. 8, pp. 317-327.
Luo, M. et al., "Repurposing endogenous type I CRISPR-Cas systems for programmable gene repression", Nucleic Acid Research (2014) 8 pages.
Magadan et al. "Cleavage of Phage DNA by the *Streptococcus thermophlius* CRISPR3-Cas System". PLoS One (2012) 7:e40913. 8 pages.
Mahillon J. et al. "Insertion sequences", Microbiol Mol Biol Rev (1998) vol. 62(3): pp. 725-774.
Makarova and Koonin "Annotation and Classification of CRISPR-Cas Systems", Methods Mol Biol. (2015), 1311: pp. 47-75.
Makarova et al. "An updated evolutionary classification of CRISPR-Cas systems", Nat Rev Microbiol. 13:722-736 (2015), 15 pages.
Makarova et al. "Unification of Cas protein families and a simple scenario for the origin and evolution of CRISPRCas systems", Biol Direct. (2011) vol. 6:38, 27 pages.
Makarova, K. S. et al. "Evolution and classification of the CRISPR-Cas systems", Nat Rev Microbiol (2011) vol. 9, pp. 467-477.

Marcotte, H. et al. "Proteomes—Lactobacillus gasseri DSM 14869", NCBI Reference Sequence CP006803, (2013) URL: https://www.uniprot.org/proteomes/UP000217220, retrieved Jul. 20, 2018.
Marraffini and Sontheimer "CRISPR Interference Limits Horizontal Gene Transfer in *Staphylococci* by Targeting DNA", Science (2008) vol. 322: pp. 1843-1845.
Mojica, F. et al. "Short motif sequences determine the targets of the prokaryotic CRISPR defence system", Microbiology (2009) vol. 155, 8 pages.
Nale Janet Y. et al., "Diverse temperate bacteriophage carriage in Clostridium difficile 027 strains", PLoS One, 7(5) 1-9 (2012).
Nishimasu, H., et al. "Crystal Structure of Cas9 in Complex with Guide RNA and Target DNA", Cell (2014) vol. 156, pp. 935-949.
Notification and Transmittal of International Search Report and Written Opinion of the International Searching Authority for International Application No. PCT/IB2015/052515; dated Oct. 10, 2015; 12 pages.
Notification of International Preliminary Report on Patentability corresponding to International Application No. PCT/IB2015/052515; dated Oct. 12, 2016, 7 pages.
Notification of Transmittal of the International Search Report and the Written Opinion of the International Searching Authority, or the Declaration, PCT/US2016/034812, dated Sep. 15, 2016, 9 pages.
Novagen "pCDF-1b Vector" Sep. 10, 2003, Retrieved from the Internet on Sep. 1, 2015, at http://www.helmholtz-muenchen.de/fieadmin/PEPF/pCDF_vectors/pCDF-1b_map.pdf, 2 pages.
Oh JH and van Pijkeren JP "CRISPR-Cas9-assisted recombineering in Lactobacillus reuteri", Nucleic Acids Res (2014) vol. 10.1093/nar/gku623.
Qi, L. S. et al. "Repurposing CRISPR as an RNA-Guided Platform for Sequence-Specific Control of Gene Expression", Cell 152, 1173-1183 (2013), 11 pages.
Sander JD, and Joung JK. "CRISPR-Cas systems for editing, regulating and targeting genomes", Nat. Biotechnol. (2014) vol. 32, pp. 347-355.
Sapranauskas et al. "The *Streptococcus thermophilus* CRISPR/Cas system provides immunity in *Escherichia coli*", Nucleic Acid Res. (2011) vol. 39: pp. 9275-9282.
Seed Kimberley D. et al., "A bacteriophage encodes its own CRISPR/Cas adaptive response to evade hose innate immunity", Nature. 494:7438, pp. 489-491 (2013).
Selle K. Barrangou R. "Harnessing CRISP-Cas systems for bacterial genome editing", Cell Press: Trends Microbiol. (2015) vol. 23(4): pp. 225-232.
Selle, K. et al. "CRISPR-based screening of genomic island excision events in bacteria", Proc Natl Acad Sci USA, (2015): 112(26): pp. 8076-8081.
Selle, K. et al., "CRISPR-Based Technologies and the Future of Food Science", Journal of Food Science (2015) vol. 80. 6 pages.
Semenova et al. "Interference by clustered regularly interspaced short palindromic repeat (CRISPR) RNA is governed by a seed sequence", PNAS. 108:25 (2011) 6 pages.
Sinkuna, T. et al. "In vitro reconstruction of Cascade-mediated CRISPR immunity in *Streptococcus thermophilus*", The EMBO Journal (2013) vol. 32, pp. 385-394.
Stern, A. et al., "Self-targeting by CRISPR: gene regulation of autoimmunity", Cell Press: Trends in Genetics, (2010) vol. 26, No. 8, 6 pages.
Sternberg et al. "DNA interrogation by the CRISPR RNA-guided endonuclease Cas9", Nature, vol. 507, (2014) 17 pages.
Terns and Terns "CRISPR-based adaptive immune systems", Curr. Opin. Microbiol. (2011) vol. 14: pp. 321-327.
Uchiyama Jumpei et al., "Characterization of Helicobacter pylori bacteriophage KHP30", Applied and environmental microbiology, 79(10):3176-3184 (2013).
Vercoe RB, et al. "Cytotoxic chromosomal targeting by CRISPR/Cas systems can reshape bacterial genomes and expel or remodel pathogenicity islands", PLoS Genet (2013) vol. 9(4):e1003454.
Westra et al. "The CRISPRs, They Are A-Changin': How Prokaryotes Generate Adaptive Immunity", Annu. Rev. Genet. (2012) vol. 46: pp. 311-339.

(56) References Cited

OTHER PUBLICATIONS

Wiedenheft et al. "RNA-guided complex from a bacterial immune system enhances target recognition through seed sequence Interactions", PNAS, 108:36 (2011) 7 pages.
Written Opinion and International Search Report corresponding to International Application No. PCT/US2016/037493, dated Sep. 15, 2016, 8 pages.
Written Opinion of the International Search Report regarding International Application No. PCT/US2016/067657, dated Mar. 6, 2017, 9 pages.
GenBank Accession AEB74124.1, "CRISPR-associated protein. Csn1 family [Lactobacillus buchneri" Oct. 11, 2011.
Cong et al. Supplementary Materials for "Multiplex Genome Engineering Using CRISPR/Cas Systems" Science, 339(6121):819-823 (2013).
Office Action, U.S. Appl. No. 15/113,656, dated Mar. 11, 2019, 22 pages.
Milani C et al. Genomic encyclopedia of type strains of the genus *Bifidobacterium*. Applied and Environmental Microbiology. Oct. 2014; 80(20): 6290-6302.
Database GenBank [online]. NBI, U.S. National Library of Medicine. Aug. 5, 2014. "CRISPER-associated protein. Csn1 family [Bifidobacterium bombi DSM 19703]." XP002785852, retrieved from NCBI accession No. GenBank: KFF31259. Database accession No. KFF31259. 1 page.
Beloglazova et al. "Structure and activity of the Cas3 HD nuclease MJ0384, an effector enzyme of the CRISPR Interference" The EMBO Journal, 30(22):4616-4627 (2011).
Final Office Action, U.S. Appl. No. 16/153,052, dated Dec. 26, 2018, 14 pages.
Final Office Action, U.S. Appl. No. 15/507,176, dated Jan. 16, 2019, 19 pages.
Claesson MJ et al. NCBI reference sequence NC_007929, direct submission Dec. 16, 2005, p. 1 (2005).
International Search Report and Written Opinion corresponding to PCT/US2019/52861, dated Feb. 12, 2020, 18 pages.
Gasiunas et al. "Molecular mechanisms of CRISPR-mediated microbial immunity" Cellular and Molecular Life Sciences, 71:449-465 (2014).
Westra et al. "CRISPR Immunity Relies on the Consecutive Binding and Degradation of Negatively Supercoiled Invader DNA by Cascade and Cas3" Molecular Cell, 46:595-605 (2012).
Hidalgo-Cantabrana et al. "Genome editing using the endogenous type I CRISPR-Cas system in Lactobacillus crispatus" PNAS, 116)32):15774-15783 (2019).
Yosef et al. "High-temperature protein G is essential for activity of the *Escherichia coli* clustered regularly interspaced short palindromic repeats (CRISPR)/Cas system" Proc Natl Acad Sci, 108(50):20136-20141 (2011).
Sanozky-Dawes et al. "Occurrence and activity of a type II CRISPR-Cas system in Lactobacillus gasseri" Microbiology, 161:1752-1761 2015.
Anderson et al., "Lactobacillus gasseri CRISPR-Cas9 characterization In Vitro reveals a flexible mode of protospacer-adjacent motif recognition" PLOS ONE, 13(2) 14 pages 2018.
International Preliminary Report on Patentability Notification, PCT/US2018/034322, dated Dec. 5, 2019, 7 pages.
GenBank Accession No. FN692037.1, "Lactobacillus crispatus ST1 complete genome, strain ST1" Feb. 27, 2015.
Ojala et al. "Comparative genomics of Lactobacillus crispatus suggests novel mechanisms for the competitive exclusion of Garnerella vaginalis" BNC Genomics, 15:1070 (2014).
International Search Report and Written Opinion corresponding to PCT/US2019/52883, dated Dec. 23, 2019, 9 pages.
International Search Report and Written Opinion corresponding to PCT/US2019/52878, dated Dec. 27, 2019, 14 pages.
International Search Report and Written Opinion corresponding to PCT/US2019/52864, dated Dec. 17, 2019, 15 pages.
Ramakrishna Suresh et al., "Gene disruption by cell-penetrating peptide-mediated delivery of Cas9 protein and guide RNA", Genome Research, 24:1020-1027 (2014).
Edgar et al. Supplemental Material "The *Escherichia coli* CRISPR System Protects from Lysogenization, Lysogens, and Prophage Induction" Journal of Bacteriology, 192(23): 6292-6294 2010.
Shinkai "Structure and Function of CRISPR-Cas System" Seibutsu Butsuri, 54(5):247-252 (2014) Abstract Only.
Extended European Search Report regarding European Application No. EP19196063, dated Jun. 26, 2020 12 pages.
Third Party Observations corresponding to European Patent Application No. 16804164.8, dated Jul. 24, 2019 60 pages.
Third Party Observations corresponding to European Patent Application No. 16812275.2, dated May 15, 2020 108 pages.
Chauthaiwale, V. M. et al. "Bacteriophage Lamda as a Cloning Vector" Microbiological Reviews, 56(4):577-591 (1992).
Dang, Y. et al. "Optimizing sgRNA structure to improve CRISPR-Cas9 knockout efficiency" Genome Biology, 16(280):1-10 (2015).
Edgar, R. et al. "Reversing Bacterial Resistance to Antibiotics by Phage-Mediated Delivery of Dominant Sensitive Genes" Applied and Environmental Microbiology, 78(3):744-751 (2011).
Extended European Search Report corresponding to European Patent Application No. 18806333.3 (8 pages) (dated Feb. 9, 2021).
Third Party Observation filed in European Patent Application No. 16804164.8 dated Feb. 19, 2021, 15 pages.
Third Party Observation filed in European Patent Application No. 16812275.2 dated Feb. 19, 2021, 38 pages.
Yosef, I. et al. "Temperate and lytic bacteriophages programmed to sensitize and kill antibiotic-resistant bacteria" PNAS, 112(23):7267-7272 (2015).
Luo et al. "The CRISPR RNA-guided surveillance complex in *Escherichia coli* accommodates extended RNA Spacers" Nucleic Acids Research, 44(15):7385-7394 2016.
Gutierrez et al. "Predicting CRISPR-Cas9 activity in *E. coli*" bioRxviv, https://doi.org/10.1101/308148, pp. 1-22 2018.
Hochstrassera et al. "CasA mediates Cas3-catalyzed target degradation during CRISPR RNA-guided interference" PNAS, 111(18):6618-23 2014.
Nizet et al. "Bacterial sepsis and meningitis" Remington and Klein's Infectious diseases of the fetus and newborn infant, 8th Edition, pp. 217-271 2011.
Verco et al. "Cytotoxic Chromosomal Targeting by CRISPR/Cas Systems Can Reshape Bacterial Genomes and Expel or Remodel Pathogenicity Islands" PLOS Genetics, 9(4):1-13 2013.

\* cited by examiner

| Type I | | Processed (P) or Unprocessed (U)? | CPP on 5' or 3'? |
|---|---|---|---|
| ① |  | U | Either |
| ② |  | P | 3' |
| ③ |  | P | 3' |
| ④ |  | P | 3' |

| Type II | | | CPP on 5' or 3'? |
|---|---|---|---|
| ① |  | U | Either |
| ② |  | P | Either |
| ③ |  | P | Either |

| Type III | | | CPP on 5' or 3'? |
|---|---|---|---|
| ① |  | U | Either |
| ② |  | P | 3' |
| ③ |  | P | 3' |
| ④ |  | P | 3' |

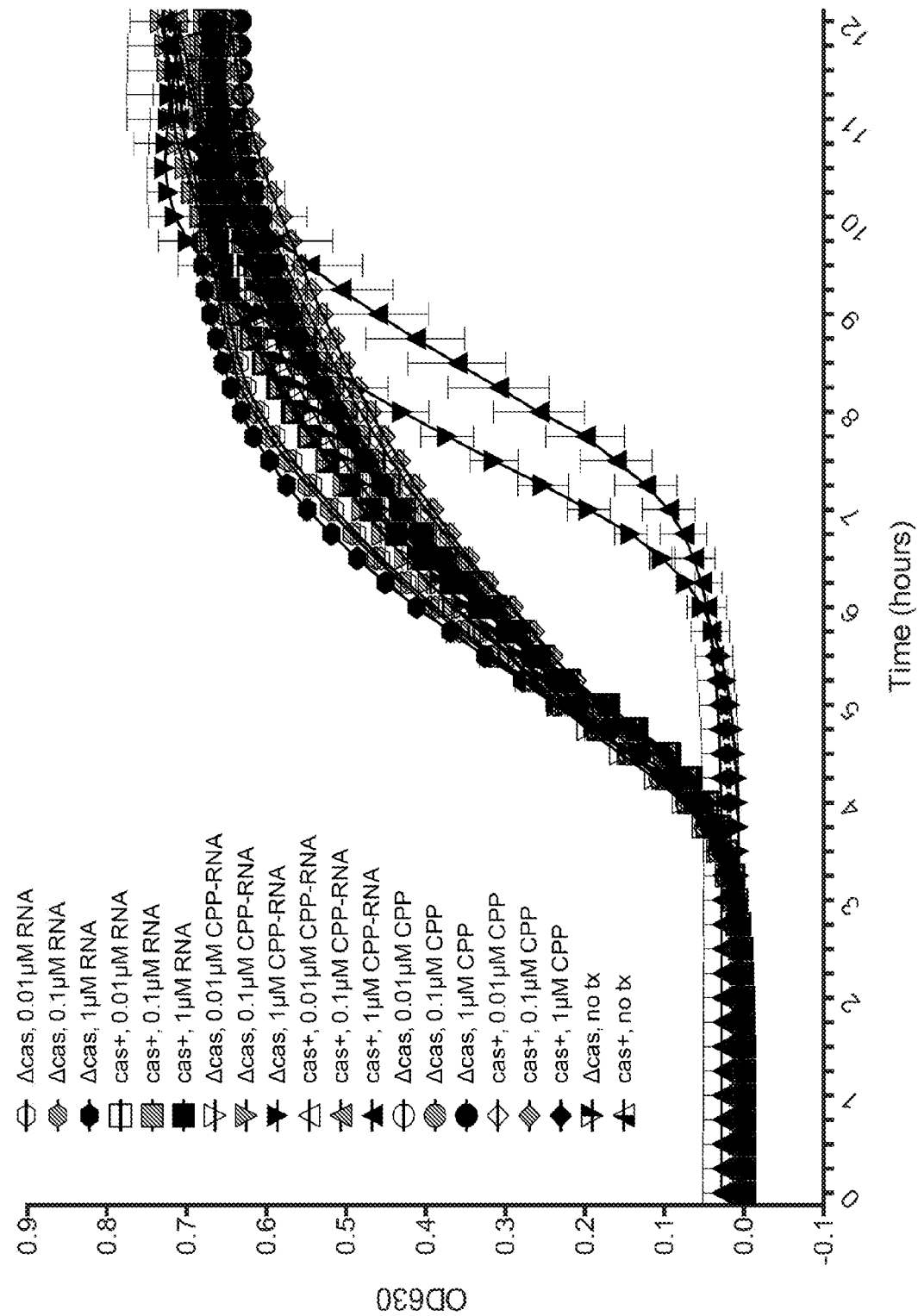

SEQUENCE LISTING

```
<160> NUMBER OF SEQ ID NOS: 52

<210> SEQ ID NO 1
<211> LENGTH: 10
<212> TYPE: PRT
<213> ORGANISM: Artificial
<220> FEATURE:
<223> OTHER INFORMATION: Cell penetrating peptide sequence

<400> SEQUENCE: 1

Lys Phe Phe Lys Phe Phe Lys Phe Phe Lys
1               5                   10

<210> SEQ ID NO 2
<211> LENGTH: 13
<212> TYPE: PRT
<213> ORGANISM: Artificial
<220> FEATURE:
<223> OTHER INFORMATION: Cell penetrating peptide sequence
<220> FEATURE:
<221> NAME/KEY: MISC_FEATURE
<222> LOCATION: (2)..(2)
<223> OTHER INFORMATION: Xaa is 6-aminocaproic acid
<220> FEATURE:
<221> NAME/KEY: MISC_FEATURE
<222> LOCATION: (5)..(5)
<223> OTHER INFORMATION: Xaa is 6-aminocaproic acid
<220> FEATURE:
<221> NAME/KEY: MISC_FEATURE
<222> LOCATION: (8)..(8)
<223> OTHER INFORMATION: Xaa is 6-aminocaproic acid
<220> FEATURE:
<221> NAME/KEY: MISC_FEATURE
<222> LOCATION: (11)..(11)
<223> OTHER INFORMATION: Xaa is 6-aminocaproic acid
<220> FEATURE:
<221> NAME/KEY: MISC_FEATURE
<222> LOCATION: (13)..(13)
<223> OTHER INFORMATION: Xaa is b-alanine
```

```
<400> SEQUENCE: 2

Arg Xaa Arg Arg Xaa Arg Arg Xaa Arg Arg Xaa Arg Xaa
1               5                   10

<210> SEQ ID NO 3
<211> LENGTH: 7
<212> TYPE: PRT
<213> ORGANISM: Artificial
<220> FEATURE:
<223> OTHER INFORMATION: Cell penetrating peptide sequence

<400> SEQUENCE: 3

Pro Lys Lys Lys Arg Lys Val
1               5

<210> SEQ ID NO 4
<211> LENGTH: 13
<212> TYPE: PRT
<213> ORGANISM: Artificial
<220> FEATURE:
<223> OTHER INFORMATION: Cell penetrating peptide sequence
<220> FEATURE:
<221> NAME/KEY: MISC_FEATURE
<222> LOCATION: (2)..(2)
<223> OTHER INFORMATION: Xaa is 6-aminohexanoic acid
<220> FEATURE:
<221> NAME/KEY: MISC_FEATURE
<222> LOCATION: (5)..(5)
<223> OTHER INFORMATION: Xaa is 6-aminohexanoic acid
<220> FEATURE:
<221> NAME/KEY: MISC_FEATURE
<222> LOCATION: (8)..(8)
<223> OTHER INFORMATION: Xaa is 6-aminohexanoic acid
<220> FEATURE:
<221> NAME/KEY: MISC_FEATURE
<222> LOCATION: (11)..(11)
<223> OTHER INFORMATION: Xaa is 6-aminohexanoic acid
<220> FEATURE:
<221> NAME/KEY: MISC_FEATURE
<222> LOCATION: (13)..(13)
<223> OTHER INFORMATION: Xaa is b-alanine

<400> SEQUENCE: 4

Arg Xaa Arg Arg Xaa Arg Arg Xaa Arg Arg Xaa Arg Xaa
1               5                   10

<210> SEQ ID NO 5
<211> LENGTH: 16
<212> TYPE: PRT
<213> ORGANISM: Artificial
<220> FEATURE:
<223> OTHER INFORMATION: Cell penetrating peptide sequence

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Artificial
<220> FEATURE:
<223> OTHER INFORMATION: Cell penetrating peptide sequence

<400> SEQUENCE: 6

Arg Lys Lys Arg Arg Gln Arg Arg Arg
1               5
```

```
<210> SEQ ID NO 7
<211> LENGTH: 24
<212> TYPE: PRT
<213> ORGANISM: Artificial
<220> FEATURE:
<223> OTHER INFORMATION: Cell penetrating peptide sequence

<400> SEQUENCE: 7

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 8
<211> LENGTH: 10
<212> TYPE: PRT
<213> ORGANISM: Artificial
<220> FEATURE:
<223> OTHER INFORMATION: Cell penetrating peptide sequence

<400> SEQUENCE: 8

Val Gln Arg Lys Arg Gln Lys Leu Met Pro
1               5                   10

<210> SEQ ID NO 9
<211> LENGTH: 8
<212> TYPE: PRT
<213> ORGANISM: Artificial
<220> FEATURE:
<223> OTHER INFORMATION: Cell penetrating peptide sequence

<400> SEQUENCE: 9

Ser Lys Lys Lys Lys Thr Lys Val
1               5

<210> SEQ ID NO 10
<211> LENGTH: 8
<212> TYPE: PRT
<213> ORGANISM: Artificial
<220> FEATURE:
<223> OTHER INFORMATION: Cell penetrating peptide sequence

<400> SEQUENCE: 10

Gly Arg Lys Arg Lys Lys Arg Thr
1               5

<210> SEQ ID NO 11
<211> LENGTH: 9
<212> TYPE: PRT
<213> ORGANISM: Artificial
<220> FEATURE:
<223> OTHER INFORMATION: Cell penetrating peptide sequence

<400> SEQUENCE: 11

Arg Arg Arg Glu Arg Arg Ala Glu Lys
1               5

<210> SEQ ID NO 12
<211> LENGTH: 9
<212> TYPE: PRT
<213> ORGANISM: Artificial
<220> FEATURE:
<223> OTHER INFORMATION: Cell penetrating peptide sequence

<400> SEQUENCE: 12

Lys Cys Pro Ser Arg Arg Pro Lys Arg
1               5
```

<210> SEQ ID NO 13
<211> LENGTH: 18
<212> TYPE: PRT
<213> ORGANISM: Artificial
<220> FEATURE:
<223> OTHER INFORMATION: Cell penetrating peptide sequence

<400> SEQUENCE: 13

Val Arg Leu Pro Pro Val His Leu Pro Pro Val Lys Leu Pro
1               5                   10                  15

Pro Pro

<210> SEQ ID NO 14
<211> LENGTH: 17
<212> TYPE: PRT
<213> ORGANISM: Artificial
<220> FEATURE:
<223> OTHER INFORMATION: Cell penetrating peptide sequence

<400> SEQUENCE: 14

Ala Val Gly Ala Ile Gly Ala Leu Phe Leu Gly Phe Leu Gly Ala Ala
1               5                   10                  15

Gly

<210> SEQ ID NO 15
<211> LENGTH: 12
<212> TYPE: PRT
<213> ORGANISM: Artificial
<220> FEATURE:
<223> OTHER INFORMATION: Cell penetrating peptide sequence

<400> SEQUENCE: 15

Pro Leu Ser Ser Ile Phe Ser Arg Ile Gly Asp Pro
1               5                   10

<210> SEQ ID NO 16
<211> LENGTH: 16
<212> TYPE: PRT
<213> ORGANISM: Artificial
<220> FEATURE:
<223> OTHER INFORMATION: Cell penetrating peptide sequence

<400> SEQUENCE: 16

Ala Ala Val Ala Leu Leu Pro Ala Val Leu Leu Ala Leu Leu Ala Pro
1               5                   10                  15

<210> SEQ ID NO 17
<211> LENGTH: 15
<212> TYPE: PRT
<213> ORGANISM: Artificial
<220> FEATURE:
<223> OTHER INFORMATION: Cell penetrating peptide sequence

<400> SEQUENCE: 17

Val Thr Val Leu Ala Leu Gly Ala Leu Ala Gly Val Gly Val Gly
1               5                   10                  15

<210> SEQ ID NO 18
<211> LENGTH: 18
<212> TYPE: PRT
<213> ORGANISM: Artificial
<220> FEATURE:
<223> OTHER INFORMATION: Cell penetrating peptide sequence

<400> SEQUENCE: 18

```
Ile Ala Ala Arg Ile Lys Leu Arg Ser Arg Gln His Ile Lys Leu Arg
1               5                   10                  15

His Leu

<210> SEQ ID NO 19
<211> LENGTH: 27
<212> TYPE: PRT
<213> ORGANISM: Artificial
<220> FEATURE:
<223> OTHER INFORMATION: Cell penetrating peptide sequence

<400> SEQUENCE: 19

Asp Thr Trp Pro Gly Val Glu Ala Leu Ile Arg Ile Leu Gln Gln Leu
1               5                   10                  15

Leu Phe Ile His Phe Arg Ile Gly Cys Gln His
            20                  25

<210> SEQ ID NO 20
<211> LENGTH: 27
<212> TYPE: PRT
<213> ORGANISM: Artificial
<220> FEATURE:
<223> OTHER INFORMATION: Cell penetrating peptide sequence

<400> SEQUENCE: 20

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25

<210> SEQ ID NO 21
<211> LENGTH: 28
<212> TYPE: PRT
<213> ORGANISM: Artificial
<220> FEATURE:
<223> OTHER INFORMATION: Cell penetrating peptide sequence

<400> SEQUENCE: 21

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 22
<211> LENGTH: 21
<212> TYPE: PRT
<213> ORGANISM: Artificial
<220> FEATURE:
<223> OTHER INFORMATION: Cell penetrating peptide sequence

<400> SEQUENCE: 22

Thr Arg Ser Ser Arg Ala Gly Leu Gln Trp Pro Val Gly Arg Val His
1               5                   10                  15

Arg Leu Leu Arg Lys
            20

<210> SEQ ID NO 23
<211> LENGTH: 23
<212> TYPE: PRT
<213> ORGANISM: Artificial
<220> FEATURE:
<223> OTHER INFORMATION: Cell penetrating peptide sequence

<400> SEQUENCE: 23
```

```
Gly Ile Gly Lys Phe Leu His Ser Ala Lys Lys Trp Gly Lys Ala Phe
1               5                   10                  15

Val Gly Gln Ile Met Asn Ser
            20
```

<210> SEQ ID NO 24
<211> LENGTH: 37
<212> TYPE: PRT
<213> ORGANISM: Artificial
<220> FEATURE:
<223> OTHER INFORMATION: Cell penetrating peptide sequence

<400> SEQUENCE: 24

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35
```

<210> SEQ ID NO 25
<211> LENGTH: 18
<212> TYPE: PRT
<213> ORGANISM: Artificial
<220> FEATURE:
<223> OTHER INFORMATION: Cell penetrating peptide sequence

<400> SEQUENCE: 25

```
Arg Gly Gly Arg Leu Ser Tyr Ser Arg Arg Arg Phe Ser Thr Ser Thr
1               5                   10                  15

Gly Arg
```

<210> SEQ ID NO 26
<211> LENGTH: 10
<212> TYPE: PRT
<213> ORGANISM: Artificial
<220> FEATURE:
<223> OTHER INFORMATION: Cell penetrating peptide sequence

<400> SEQUENCE: 26

```
Arg Arg Leu Ser Tyr Ser Arg Arg Arg Phe
1               5                   10
```

<210> SEQ ID NO 27
<211> LENGTH: 33
<212> TYPE: PRT
<213> ORGANISM: Artificial
<220> FEATURE:
<223> OTHER INFORMATION: Cell penetrating peptide sequence

<400> SEQUENCE: 27

```
Ala Leu Trp Lys Thr Leu Leu Lys Lys Val Leu Lys Ala Ala Leu Trp
1               5                   10                  15

Lys Thr Leu Leu Lys Lys Val Leu Lys Ala Pro Lys Lys Lys Arg Lys
            20                  25                  30

Val
```

<210> SEQ ID NO 28
<211> LENGTH: 10
<212> TYPE: PRT
<213> ORGANISM: Artificial
<220> FEATURE:
<223> OTHER INFORMATION: Cell penetrating peptide sequence

```
<400> SEQUENCE: 28

Pro Arg Pro Leu Pro Phe Pro Arg Pro Gly
1               5                   10

<210> SEQ ID NO 29
<211> LENGTH: 27
<212> TYPE: PRT
<213> ORGANISM: Artificial
<220> FEATURE:
<223> OTHER INFORMATION: Cell penetrating peptide sequence

<400> SEQUENCE: 29

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 30
<211> LENGTH: 8
<212> TYPE: PRT
<213> ORGANISM: Artificial
<220> FEATURE:
<223> OTHER INFORMATION: Cell penetrating peptide sequence

<400> SEQUENCE: 30

Arg Arg Arg Arg Arg Arg Arg Arg
1               5

<210> SEQ ID NO 31
<211> LENGTH: 18
<212> TYPE: PRT
<213> ORGANISM: Artificial
<220> FEATURE:
<223> OTHER INFORMATION: Cell penetrating peptide sequence

<400> SEQUENCE: 31

Lys Leu Ala Leu Lys Leu Ala Leu Lys Ala Leu Lys Ala Ala Leu Lys
1               5                   10                  15

Leu Ala

<210> SEQ ID NO 32
<211> LENGTH: 11
<212> TYPE: PRT
<213> ORGANISM: Artificial
<220> FEATURE:
<223> OTHER INFORMATION: Cell penetrating peptide sequence

<400> SEQUENCE: 32

Tyr Ala Arg Ala Ala Ala Arg Gln Ala Arg Ala
1               5                   10

<210> SEQ ID NO 33
<211> LENGTH: 27
<212> TYPE: PRT
<213> ORGANISM: Artificial
<220> FEATURE:
<223> OTHER INFORMATION: Cell penetrating peptide sequence

<400> SEQUENCE: 33

Asp Pro Lys Gly Asp Pro Lys Gly Val Thr Val Thr Val Thr Val
1               5                   10                  15

Thr Val Thr Gly Lys Gly Asp Pro Lys Pro Asp
            20                  25
```

<210> SEQ ID NO 34
<211> LENGTH: 16
<212> TYPE: PRT
<213> ORGANISM: Artificial
<220> FEATURE:
<223> OTHER INFORMATION: Cell penetrating peptide sequence

<400> SEQUENCE: 34

```
Lys Lys Trp Lys Met Arg Arg Asn Gln Phe Trp Val Arg Val Gln Arg
1               5                   10                  15
```

<210> SEQ ID NO 35
<211> LENGTH: 17
<212> TYPE: PRT
<213> ORGANISM: Artificial
<220> FEATURE:
<223> OTHER INFORMATION: Cell penetrating peptide sequence

<400> SEQUENCE: 35

```
Arg Arg Trp Arg Arg Trp Trp Trp Arg Arg Trp Trp Arg Arg Trp Arg
1               5                   10                  15

Arg
```

<210> SEQ ID NO 36
<211> LENGTH: 28
<212> TYPE: PRT
<213> ORGANISM: Artificial
<220> FEATURE:
<223> OTHER INFORMATION: Cell penetrating peptide sequence

<400> SEQUENCE: 36

```
Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val Cys
            20                  25
```

<210> SEQ ID NO 37
<211> LENGTH: 21
<212> TYPE: PRT
<213> ORGANISM: Artificial
<220> FEATURE:
<223> OTHER INFORMATION: Cell penetrating peptide sequence

<400> SEQUENCE: 37

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 38
<211> LENGTH: 136
<212> TYPE: PRT
<213> ORGANISM: Artificial
<220> FEATURE:
<223> OTHER INFORMATION: Cell penetrating peptide sequence

<400> SEQUENCE: 38

```
Thr Pro Pro Lys Lys Lys Arg Lys Val Glu Asp Pro Lys Lys Lys Lys
1               5                   10                  15

Lys Thr Pro Pro Lys Lys Lys Arg Lys Val Glu Asp Pro Lys Lys Lys
            20                  25                  30

Lys Lys Thr Pro Pro Lys Lys Lys Arg Lys Val Glu Asp Pro Lys Lys
        35                  40                  45
```

```
Lys Lys Lys Thr Pro Pro Lys Lys Arg Lys Val Glu Asp Pro Lys
 50                  55                  60
Lys Lys Lys Lys Thr Pro Pro Lys Lys Arg Lys Val Glu Asp Pro
 65                  70                  75                  80
Lys Lys Lys Lys Lys Thr Pro Pro Lys Lys Arg Lys Val Glu Asp
                 85                  90                  95
Pro Lys Lys Lys Lys Thr Pro Pro Lys Lys Arg Lys Val Glu
            100                 105                 110
Asp Pro Lys Lys Lys Lys Thr Pro Pro Lys Lys Arg Lys Val
        115                 120                 125
Glu Asp Pro Lys Lys Lys Lys
    130                 135

<210> SEQ ID NO 39
<211> LENGTH: 30
<212> TYPE: PRT
<213> ORGANISM: Artificial
<220> FEATURE:
<223> OTHER INFORMATION: Cell penetrating peptide sequence

<400> SEQUENCE: 39

Ser Asp Leu Trp Glu Met Met Met Val Ser Leu Ala Cys Gln Tyr Gly
 1               5                  10                  15
Glu Ala His Ile Pro Thr Ser Glu Met Arg Glu Lys Gly Trp
             20                  25                  30

<210> SEQ ID NO 40
<211> LENGTH: 63
<212> TYPE: DNA
<213> ORGANISM: Artificial
<220> FEATURE:
<223> OTHER INFORMATION: alpha-ftsA CRISPR RNA

<400> SEQUENCE: 40
auaaaccgcu gaaguagaaa aacguguuac agcaucaguu gaguucgccg cgcgagcggg      60
gau                                                                   63

<210> SEQ ID NO 41
<211> LENGTH: 84
<212> TYPE: DNA
<213> ORGANISM: Artificial
<220> FEATURE:
<223> OTHER INFORMATION: alpha-ftsA repeat-spacer-repeat

<400> SEQUENCE: 41
gaguuccccg cgcgagcggg gauaaaccgc ugaaguagaa aacguguuua cagcaucagu      60 ugaguuccccc gcgcgagcgg ggau                                            84

<210> SEQ ID NO 42
<211> LENGTH: 63
<212> TYPE: DNA
<213> ORGANISM: Artificial
<220> FEATURE:
<223> OTHER INFORMATION: alpha-mviM CRISPR RNA

<400> SEQUENCE: 42
```

```
auaaaccgag cgcgggcagg guauucucau caaacccauc gaguuccccg cgcgagcggg    60
gau                                                                 63

<210> SEQ ID NO 43
<211> LENGTH: 86
<212> TYPE: DNA
<213> ORGANISM: Artificial
<220> FEATURE:
<223> OTHER INFORMATION: alpha-ftsA repeat-spacer-repeat

<400> SEQUENCE: 43
uugaguuccc cgcgcgagcg gggauaaacc gagcgcgggc aggguauucu caucaaaccc    60
aucgaguucc ccgcgcgagc ggggau                                        86

<210> SEQ ID NO 44
<211> LENGTH: 56
<212> TYPE: DNA
<213> ORGANISM: Artificial
<220> FEATURE:
<223> OTHER INFORMATION: CPP peptide coding sequence

<400> SEQUENCE: 44
uaacgcgguc gccaaagaga guuuuagagc ugugcuguuu ugaauggucc caaaac        56

<210> SEQ ID NO 45
<211> LENGTH: 56
<212> TYPE: DNA
<213> ORGANISM: Artificial
<220> FEATURE:
<223> OTHER INFORMATION: alpha-dnaE CRISPR RNA

<400> SEQUENCE: 45
aucagcuccu uuucucggcc guuuuguac ucucaagauu uaaguaacug uacaac         56

<210> SEQ ID NO 46
<211> LENGTH: 56
<212> TYPE: DNA
<213> ORGANISM: Artificial
<220> FEATURE:
<223> OTHER INFORMATION: alpha-mviM CRISPR RNA

<400> SEQUENCE: 46
guauucucau caaacccauc guuuuguac ucucaagauu uaaguaacug uacaac         56

<210> SEQ ID NO 47
<211> LENGTH: 56
<212> TYPE: DNA
<213> ORGANISM: Artificial
<220> FEATURE:
<223> OTHER INFORMATION: alpha-dnaE CRISPR RNA

<400> SEQUENCE: 47
acaaccucuc ucaaccgucc guuuuggaac cauucgaaac aacacagcuc uaaaac        56

<210> SEQ ID NO 48
<211> LENGTH: 56
<212> TYPE: DNA
<213> ORGANISM: Artificial
<220> FEATURE:
<223> OTHER INFORMATION: alpha-mviM CRISPR RNA

<400> SEQUENCE: 48
guauucucau caaacccauc guuuuggaac cauucgaaac aacacagcuc uaaaac        56
```

```
<210> SEQ ID NO 49
<211> LENGTH: 46
<212> TYPE: DNA
<213> ORGANISM: Artificial
<220> FEATURE:
<223> OTHER INFORMATION: alpha-pGO CRISPR RNA

<400> SEQUENCE: 49
acgagaacac guaugccgaa guauauaaau caucaguaca aaggat              46

<210> SEQ ID NO 50
<211> LENGTH: 107
<212> TYPE: DNA
<213> ORGANISM: Artificial
<220> FEATURE:
<223> OTHER INFORMATION: alpha-pGO CRISPR RNA

<400> SEQUENCE: 50
gaucgauacc caccccgaag aaaaggggac gagaacacgu augccgaagu auauaaauca    60
ucaguacaaa ggaucgauac ccaccccgaa gaaaagggga cgagaac               107

<210> SEQ ID NO 51
<211> LENGTH: 46
<212> TYPE: DNA
<213> ORGANISM: Artificial
<220> FEATURE:
<223> OTHER INFORMATION: alpha-mviM CRISPR RNA

<400> SEQUENCE: 51
acgagaacag cgcgggcagg guauucucau caaacccauc agagat              46

<210> SEQ ID NO 52
<211> LENGTH: 107
<212> TYPE: DNA
<213> ORGANISM: Artificial
<220> FEATURE:
<223> OTHER INFORMATION: alpha-mviM CRISPR RNA

<400> SEQUENCE: 52
gaucgauacc caccccgaag aaaaggggac gagaacagcg cgggcagggu auucucauca    60
aacccaucag agaucgauac ccaccccgaa gaaaagggga cgagaac               107
```

METHODS AND COMPOSITIONS FOR SEQUENCE SPECIFIC ANTIMICROBIALS

STATEMENT OF PRIORITY

This application claims the benefit, under 35 U.S.C. § 119(e), of U.S. Provisional Application No. 62/233,762 filed on Sep. 28, 2015, the entire contents of which is incorporated by reference herein.

FIELD OF THE INVENTION

The invention relates to compositions for killing cells comprising cell-penetrating peptides linked to CRISPR RNAs and methods for their use. In some aspects, the compositions include antimicrobial compositions

BACKGROUND OF THE INVENTION

The discovery of antibiotics in the 1940's ushered in a new era of modern medicine. However, their use was quickly followed by reports of antibiotic-resistant infections. Historically, these instances were rare and secluded, yet reports of antibiotic resistance in the US and worldwide have become increasingly common (Gootz, T. D. *Crit. Rev. Immunol.* 30, 79-93 (2010)). A number of underlying forces have been blamed, including the overuse of antibiotic drugs, the existence of single genes that block the action of broad classes of small-molecule antibiotics, and the ability of these genes to be passed between unrelated bacteria via mobile genetic elements. Regardless of the underlying causes, the problem of antibiotic resistance grows with each passing year, with recent calls by the World Health Organization and the Office of the President to develop novel and sustainable solutions.

Aside from multidrug resistance, a separate issue is the broad-spectrum nature of antibiotics. While this attribute allows antibiotics to be administered without detailed knowledge of the infectious agent, the antibiotics also clear a wide range of resident bacteria, which are now known to confer both immediate and long-term health benefits to their host, whether by providing additional nutrient sources, training the immune system, or fending off pathogens (Doron et al. *Expert Rev. Anti Infect. Ther.* 4, 261-275 (2006) and Matos et al. *Microb. Cell Factories* 13 Suppl 1, S6 (2014)). One consequence is that antibiotic treatment can lead to infections by opportunistic pathogens such as *Clostridium difficile* (Mathur et al. *Gut Microbes* 5, 696-710 (2014)), which are increasingly resistant to antibiotic treatment and require fecal transplants that are unsettling and pose uncertainties about the long-term impact of the introduced microbiome.

The present invention overcomes previous shortcomings in the art by providing compositions and methods of use that can circumvent commonly transmitted modes of drug resistance, including antimicrobials that can be programmed to spare beneficial bacteria.

SUMMARY OF THE INVENTION

In a first aspect, the invention provides a chimeric construct comprising a cell penetrating peptide (CPP) linked to a CRISPR (Clustered Regularly Interspaced Short Palindromic Repeats) RNA (crRNA). The crRNA may be a Type-I crRNA, Type-II crRNA or Type III crRNA In a second aspect, an antimicrobial composition is provided, comprising a chimeric construct of the invention and a carrier.

In a third aspect, a pharmaceutical composition is provided, comprising a chimeric construct of the invention in a pharmaceutically acceptable carrier.

In a fourth aspect, a method of killing a target cell comprising: contacting the target cell with an effective amount of the chimeric construct of the invention, the antimicrobial composition of the invention and/or the pharmaceutical composition of the invention, thereby killing the target cell.

In a fifth aspect, a method of killing a target bacterial cell and/or a target archaeal cell is provided, comprising: contacting the target bacterial cell and/or target archaeal cell with an effective amount of the chimeric construct of the invention, the antimicrobial composition of the invention and/or the pharmaceutical composition of the invention, thereby killing the target bacterial cell and/or target archaeal cell.

In a sixth aspect a method of treating a bacterial infection in a subject in need thereof is provided, the method comprising: administering to the subject an effective amount of the pharmaceutical composition of the invention, thereby treating the bacterial infection.

A further aspect of the invention relates to the use of the compositions of the invention for the preparation of a medicament to treat an infection, disease, and/or condition in a subject in need thereof.

Additional aspects of the invention provide kits comprising one or more chimeric constructs of the invention, and/or a antimicrobial and/or pharmaceutical composition comprising one or more chimeric constructs of the invention, and/or a product comprising one or more chimeric constructs of the invention.

These and other aspects of the invention are set forth in more detail in the description of the invention below.

BRIEF DESCRIPTION OF THE DRAWINGS

FIGS. 2A-2C show that delivery of Type I-E CRISPR RNAs using CPPs elicits cell death in *E. coli*. FIG. 2A shows the effect of the different treatments after a 35 min incubation and FIG. 2B shows the effect of the different treatments after a 2 hr incubation. FIG. 2C shows growth curves of *E. coli* with the indicated treatments.

FIG. 3A shows the effect of the different treatments as measured by colony forming units (cfu) and FIG. 3B shows the effect of the different treatments as measured by optical density at 630 nm (increase in time to reach mid-log growth phage).

DETAILED DESCRIPTION

Figure 1:
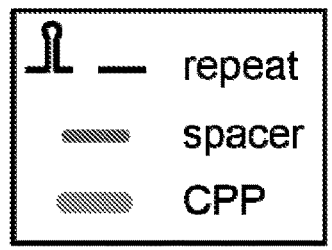
FIG. 1 shows various configurations of the chimeric construct varying the type of the CRISPR RNA (crRNA) (I, II, or III), the processed form of the crRNA, and where the cell-penetrating peptide (CPP) is attached to the crRNA. The unprocessed form consists of a repeat (thin black line), spacer (rounded line), and repeat. The processed forms vary between each type of crRNA. The CPP can be covalently coupled to the crRNA at the 3' end for all forms and at the 5' end for only some forms based on how the crRNA is processed and recognized by the Cas proteins. In cases where the CPP can be coupled to both ends of the crRNA, two CPPs could be coupled to a single crRNA (not shown).
Figure 1:
Figure 1:
Figure 1:
Figure 1:
Figure 1:
Figure 1:
Figure 1:
Figure 1:
Figure 1:
Figure 1:
Figure 1:

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "chimeric" may refer to a nucleic acid molecule and/or a polypeptide in which at least two components are derived from different sources (e.g., different organisms, different coding regions). Also as used herein, chimeric refers to a construct comprising a polypeptide linked to a nucleic acid.

"Complement" as used herein can mean 100% complementarity with the comparator nucleotide sequence or it can mean less than 100% complementarity (e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity). Complement may also be used in terms of a "complement" to or "complementing" a mutation.

The terms "complementary" or "complementarity," as used herein, refer to the natural binding of polynucleotides under permissive salt and temperature conditions by base-pairing. For example, the sequence "5'-A-G-T-3" binds to the complementary sequence "5'-A-C-T-3'." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, "contact," contacting," "contacted," and grammatical variations thereof, refers to placing the components of a desired reaction together under conditions suitable for carrying out the desired reaction (e.g., killing). Thus, as used herein, "contacting" refers to a process by which a chimeric construct (a CPP-crRNA fusion) of the present invention is delivered to a cell comprising two aspects in order to kill the cell: a target DNA having substantial complementarity to at least one spacer of a crRNA of the chimeric construct of the invention and (for Type I and II systems) flanked by a protospacer-adjacent motif, and a an active CRISPR-Cas system that recognizes the crRNA. In exemplary embodiments, contacting may comprise applying the chimeric construct (antimicrobial) to a surface (including furniture, clothes, a medical device, a plant, a subject, a food product, culture medium, soil and the like). In these cases, the chimeric construct of an aqueous solution, a spray, a cream, a gel, an aerosol, and the like. Therefore, the step of contacting may comprise contacting any substrate (solid or liquid), which is, may be or is suspected to be contaminated, with a chimeric construct of the invention or a composition thereof. Thus, a chimeric construct of the invention or a composition thereof, may be used as a therapeutic for humans or animals, for decontaminating surfaces, for decontaminating liquids (e.g., salt water, fresh water, waste water, culture media, and the like), for decontaminating individuals or locations colonized or otherwise infected by a contaminating bacterium or archaeon, for prophylaxis, treatment, and vaccine compositions, for reducing contaminating bacteria or archaea in foodstuffs (e.g., food packaging, fresh produce, processed animal products), and the like. Thus, "substrate" includes, without limitation, any subject, such as a human or an animal (contact can be in vivo or ex vivo). For example, a contaminating bacterium or archaeon may have systemically infected a subject or be present on the surface of a subject. Where the contaminating bacterium or archaeon is not on the subject, the chimeric construct of the invention or composition thereof may be delivered to the site of infection by any suitable method, for example via injection, oral administration, suppositories, and the like.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different compositions or sequentially. Concurrent administration can be carried out by mixing the compounds prior to administration, or by administering the compounds in two different compositions, for example, at the same point in time but at different anatomic sites or using different routes of administration.

"Cas9 nuclease" refers to a large group of endonucleases that catalyze the double stranded DNA cleavage in the CRISPR-Cas system. These polypeptides are well known in the art and many of their structures (sequences) are characterized (See, e.g., WO2013/176772; WO/2013/188638). The domains for catalyzing the cleavage of the double stranded DNA are the RuvC domain and the HNH domain. The RuvC domain is responsible for nicking the (−) strand and the HNH domain is responsible for nicking the (+) strand (See, e.g., Gasiunas et al. *PNAS* 109(36):E2579-E2586 (Sep. 4, 2012)).

In some embodiments, a Cas9 nuclease useful with this invention can be a Cas9 nuclease that comprises one or more of the modifications as described herein, thereby resulting in a Cas9 nuclease having one or more modified activities relative to a wild-type Cas9 nuclease or a Cas9 nuclease not so modified. In other embodiments, a Cas9 nuclease useful with this invention can be a wild-type Cas9 nuclease that is introduced into and expressed or over-expressed in the natural host bacterium. In other embodiments, a Cas9 nuclease useful with this invention can be a wild-type Cas9 nuclease that is heterologous to the host bacterium into which it is introduced.

In some embodiments, a Cas9 nuclease useful with the invention is a modified Cas9 nuclease that releases the cleaved target DNA (cleaved by the Cas9) more readily than a native Cas9 or a Cas9 that is not modified to more readily release cleaved target DNA as described herein. In some embodiments, a Cas9 nuclease modified to more readily release cleaved DNA, comprises a modified protospacer adjacent motif (PAM)-interacting domain (PIM). Modifications would reduce the affinity between Cas9 and the PAM without disrupting cleavage activity. The corresponding mutations to Cas9 can be identified by saturation mutagenesis of sites within the PIM implicated in binding the PAM as well as regions important for the folding and structural integrity of the PIM.

In some embodiments, a Cas9 nuclease useful with the invention is a modified Cas9 nuclease that rather than cleaving the double stranded target DNA provides site-specific nicking of either the (−) or the (+) strand. Thus, in some embodiments, a Cas9 nuclease can comprise a mutation in the RuvC domain, thereby providing a Cas9 that is able to nick the (+) strand of the target DNA, or a mutation in the HNH domain, thereby providing a Cas9 that is able to nick the (−) strand of the target DNA. In some embodiments, a Cas9 nuclease can be introduced as a polypeptide. In representative embodiments, a Cas9 nuclease can be introduced in a nucleic acid construct.

As used herein, "Type I polypeptide" refers to any of a Cas3 polypeptide, Cas3' polypeptide, a Cas3" polypeptide and any one or more of the Type I Clustered Regularly Interspaced Short Palindromic Repeats (CRISPR)-associated complex for antiviral defense ("Cascade") polypeptides. Thus, the term "Type I polypeptide" refers to the polypeptides that make up a Type I-A CRISPR-Cas system, a Type I-B CRISPR-Cas system, a Type I-C CRISPR-Cas system, a Type I-D CRISPR-Cas system, a Type I-E CRISPR-Cas system, and/or a Type I-F CRISPR-Cas system. Each Type-I CRISPR-Cas system comprises at least one Cas3 polypeptide. Cas3 polypeptides generally comprise both a helicase domain and an HD domain. However, in some Type I CRISPR-Cas systems, the helicase and HD domain are found in separate polypeptides, Cas3' and Cas3". In particular, Cas3' encodes the helicase domain whereas Cas3" encodes the HD domain. Consequently, because both domains are required for Cas3 function, Type I subtypes either encode Cas3 (I-C, I-D, I-E, I-F) or Cas3' and Cas3" (I-A, I-B).

As used herein, "Type I Cascade polypeptides" refers to a complex of polypeptides involved in processing of pre-crRNAs and subsequent binding to the target DNA in type I CRISPR-Cas systems. These polypeptides include, but are not limited to, the Cascade polypeptides of Type I subtypes I-A, I-B, I-C, I-D, I-E and I-F. Non-limiting examples of Type I-A polypeptides include Cas7 (Csa2), Cas8a1 (Csx13), Cas8a2 (Csx9), Cas5, Csa5, Cas6a, Cas3' and/or a Cas3". Non-limiting examples of Type I-B polypeptides include Cas6b, Cas8b (Csh1), Cas7 (Csh2) and/or Cas5. Non-limiting examples of Type-IC polypeptides include Cas5d, Cas8c (Csd1), and/or Cas7 (Csd2). Non-limiting examples of Type-ID polypeptides include Cas10d (Csc3), Csc2, Csc1, and/or Cas6d. Non-limiting examples of Type I-E polypeptides include Cse1 (CasA), Cse2 (CasB), Cas7 (CasC), Cas5 (CasD) and/or Cas6e (CasE). Non-limiting examples of Type I-F polypeptides include Cys1, Cys2, Cas7 (Cys3) and/or Cas6f (Csy4).

Type III CRISPR-Cas systems can comprise a Cas6 polypeptide, a Csm complex (e.g., Type III-A Csm) and/or a Cmr complex (e.g., Type III-B Cmr). The Csm complex is comprised of the Cas10 (or Csm1), Csm2, Csm3, Csm4, Csm5, and Csm6 polypeptides. The Cmr complex is comprised of the Cmr1, Cas10 (or Csm2), Cmr3, Cmr4, Cmr5, and Cmr6 polypeptides.

A "fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. In some embodiments, a fragment of a polynucleotide can be a functional fragment that encodes a polypeptide that retains its function (e.g., a fragment of a Cas9 polypeptide retains one or more of the activities of a native Cas9 nuclease including, but not limited to, HNH nuclease activity, RuvC nuclease activity, DNA, RNA and/ or PAM recognition and binding activities). In representative embodiments, the invention may comprise a functional fragment of a Cas9 nuclease that is encoded by a fragment of a Cas9 polynucleotide.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term in "genome" as used herein includes an organism's chromosomal/nuclear genome as well as any mitochondrial, and/or plasmid genome.

A "hairpin sequence" as used herein, is a nucleotide sequence comprising hairpins (e.g., that forms one or more hairpin structures). A hairpin (e.g., stem-loop, fold-back) refers to a nucleic acid molecule having a secondary structure that includes a region of nucleotides that form a single strand that are further flanked on either side by a double stranded-region. Such structures are well known in the art. As known in the art, the double stranded region can comprise some mismatches in base pairing or can be perfectly complementary. In some embodiments, a repeat nucleotide sequence comprises, consists essentially of, consists of a hairpin sequence that is located within the repeat nucleotide sequence (i.e., at least one nucleotide (e.g., one, two, three, four, five, six, seven, eight, nine, ten, or more) of the repeat nucleotide sequence is present on either side of the hairpin that is within the repeat nucleotide sequence). In some embodiments, a hairpin sequence can be located at the 3'end of a trans-activating CRISPR (tracr) sequence. In some embodiments, a repeat sequence comprises a hairpin sequence.

A "heterologous" or a "recombinant" nucleotide sequence is a nucleotide sequence not naturally associated with a host cell into which it is introduced, including non-naturally Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence or polypeptide of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to the nucleotide sequence or polypeptide of the invention. Thus, for example, a homologue of a repeat, a tracr sequence, a Cas9 polypeptide/polynucleotide, a Cas 3 polypeptide/polynucleotide, a Cmr polypeptide/polynucleotide, a Cascade polypeptide/polynucleotide and the like, can be about 70% homologous or more to any known repeat, tracr nucleic acid, Cas9 polypeptide/polynucleotide, Cas 3 polypeptide/polynucleotide, Cmr polypeptide/polynucleotide, or Cascade polypeptide/polynucleotide, respectively.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid is a nucleotide sequence naturally associated with a host cell into which it is introduced. Thus, for example, as used herein, the term "an endogenous restriction enzyme" means a restriction enzyme that is naturally occurring in (native to) the production host bacterium.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

A "synthetic" nucleic acid or polynucleotide, as used herein, refers to a nucleic acid or polynucleotide that is not found in nature but is constructed by the hand of man and as a consequence is not a product of nature.

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

A "protospacer sequence" refers to the target double stranded DNA and specifically to the portion of the target DNA (e.g., or target region in the genome) that is fully or substantially complementary (and hybridizes) to the spacer sequence of the CRISPR spacer-repeat sequences, CRISPR repeat-spacer-repeat sequences, and/or CRISPR arrays. In the case of Type I and II CRISPR-Cas systems, the protospacer sequence is directly flanked by a PAM. In the case of Type III systems, the protospacer sequence is flanked by a sequence that shows limited complementarity to the 5' handle of the processed crRNA.

A "sub-optimal protospacer sequence" refers to a target DNA to which a spacer is designed, wherein the spacer comprises greater than 50% complementarity and less than 100% complementarity to the protospacer sequence. The reduced complementarity can come from, for example, truncating the spacer sequence at the 5' end by up to about 5 nucleotides, introducing up to 5 mismatches within the non-seed region, or introducing up to 3 mismatches within the seed region.

A "sub-optimal PAM sequence" refers to a PAM sequence that allows DNA cleavage but at a rate that is below an optimal PAM. For instance, the optimal PAM for the *Streptococcus pyogenes* Cas9 is NGG, whereas the sub-optimal PAM for this same Cas9 is NAG. Sub-optimal PAMs are commonly identified when applying high-throughput techniques for PAM elucidation.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount. Thus, for example, contacting a surface contaminated with bacteria with the chimeric construct of the present invention can result in a reduction in bacterial load by about 10%, 15%, 20%, 25%, 30%, 35%, 40%, 45%, 50%, 55%, 60%, 65%, 70%, 75%, 80%, 85%, 90%, 95%, 97%, 98%, 99%, 100% or more as compared to a control (e.g., a surface contaminated with the same bacteria but not contacted with the chimeric construct of the present invention).

A "repeat sequence" as used herein, refers to, for example, any repeat sequence of a wild-type CRISPR locus (Type I, Type II or Type III) or a repeat sequence of a synthetic crRNA. A repeat sequence useful with this invention can be any known or later identified repeat sequence of a CRISPR locus (Type I, Type II or Type III) or it can be a synthetic repeat designed to function in a Type I, Type II or Type III CRISPR-Cas system. A repeat sequence may comprise a hairpin structure and/or a stem loop structure. Thus, in some embodiments, a repeat sequence can be identical to or substantially identical to a repeat sequence from a wild-type Type I, Type II or Type III CRISPR loci. A repeat sequence from a wild-type Type I, Type II or Type III CRISPR loci may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked to the 5' end of a spacer sequence, thereby forming a repeat-spacer sequence. In other embodiments, a repeat sequence or portion thereof is linked to the 3' end of a spacer sequence, thereby forming a spacer-repeat sequence. In further embodiments, a repeat sequence or portion thereof is linked to the 5' end and to the 3' end of a spacer sequence, thereby forming a repeat-spacer-repeat sequence.

In some embodiments, a repeat sequence comprises, consists essentially of, or consists of at least one nucleotide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides, or any range therein) depending on the CRISPR-Cas system (e.g., Type I, Type II, Type III), the particular repeat and whether the crRNA comprising the repeat is processed or unprocessed. In some embodiments, a repeat sequence comprises, consists essentially of, or consists of at least about one to about 40 nucleotides. In still other embodiments, a repeat sequence comprises, consists essentially of, or consists of at least about 8 nucleotides to about 40 nucleotides, or any range or value therein. In further embodiments, a repeat sequence can comprise, consist essentially of, or consist of about 10 nucleotides to about 40 nucleotides, about 15 nucleotides to about 40 nucleotides, about 20 nucleotides to about 40 nucleotides, about 25 nucleotides to about 40 nucleotides, about 1 to about 35 nucleotides, about 10 to about 35 nucleotides, about 15 to about 35 nucleotides, about 20 to about 35 nucleotides, about 25 to about 35 nucleotides, about 20 to about 30 nucleotides, and/or about 25 to about 30 nucleotides, or any range or value therein. In representative embodiments, a repeat sequence can comprise, consist essentially of, or consist of about 25 nucleotides to about 38 nucleotides, or any range or value therein. When more than one spacer sequence is present in a CRISPR array, each spacer nucleotide sequence is separated from another by repeat sequences.

In some embodiments, a repeat sequence linked to the 5' or to the 3' end of a spacer sequence can comprise a portion of a repeat sequence (e.g., 1, 2, 3, 4, 5, 6, 7, 8, 9, 10, 11, 12, 13, 14, 15 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type repeat nucleotide sequence. In representative embodiments, a repeat sequence linked to the 5' end of a spacer sequence can be about eight consecutive nucleotides in length and have at least 90% identity (e.g., at least about 90%, 91%, 92%, 93%, 94%, 95%, 96%, 97%, 98%, 99%, or more) to the same region (e.g., 5' end) of a wild type repeat nucleotide sequence. In representative embodiments, a repeat sequence linked to the 3' end of a spacer sequence in a crRNA for Type I system can comprise a portion of consecutive nucleotides of a Type I repeat sequence from the 5'-most end through the hairpin of the Type I repeat sequence (e.g., to the 3' end of the hairpin of the repeat sequence). In further embodiments, a repeat sequence linked to the 3' end of a spacer sequence in a crRNA for Type I system can comprise a portion of consecutive nucleotides of a Type I repeat sequence from the 5'-most end up to the base of the stem loop of the Type I repeat sequence (e.g., up to the 5' end of the stem loop structure of the repeat sequence). In still further embodiments, when a repeat sequence is linked to the 3' end of a spacer sequence in a crRNA for Type III system, the repeat can comprise at least one nucleotide of a Type III repeat sequence (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleotides of a wild-type repeat sequence, and any value or range therein), wherein when the repeat sequence of the crRNA comprises two or more nucleotides, the two or more nucleotides are consecutive nucleotides from a selected repeat sequence (e.g., a wild type or synthetic repeat sequence).

A "CRISPR RNA" or "crRNA as used herein means a nucleic acid that comprises at least one spacer sequence and at least one repeat sequence, or a portion thereof, linked to the 5' end of the spacer sequence. The design of a crRNA of this invention will vary based on the CRISPR-Cas system in which the crRNA is to be used. The crRNAs of this invention are synthetic, made by man and not found in nature. In some embodiments, a crRNA may comprise, from 5' to 3', a repeat sequence (full length or portion thereof ("handle")), a spacer sequence, and a repeat sequence (full length or portion thereof). In some embodiments, a crRNA may comprise, from 5' to 3', a repeat sequence (full length or portion thereof ("handle")) and a spacer sequence. In some embodiments, a crRNA of this invention can further comprise a tracrRNA, thereby forming a single guide RNA for a Type II CRISPR-Cas system.

In some embodiments, crRNA comprises at least one spacer sequence (having a 5' end and a 3' end) linked at its 3' end to the 5' end of at least one repeat sequence or a portion of the least one repeat sequence to form a "spacer-repeat sequence" having a 5' end and a 3' end In some embodiments, a crRNA may comprise a spacer-repeat sequence that comprises a further repeat sequence, or portion thereof, the further repeat sequence linked at its 3' end to the 5' end of a spacer-repeat sequence, thereby forming a "repeat-spacer-repeat sequence." In still further embodiments, a repeat-spacer-repeat sequence may be linked at the 3' end to at least one to up to about nine further spacer-repeat sequences (e.g., 1, 2, 3, 4, 5, 6, 7, 8, 9 additional consecutive spacer-repeat sequences). In such embodiments, each of the at least one up to nine additional consecutive spacer-repeat sequences, each having a 5' end and a 3' end, are linked at the 3' end to the 5' end of the next spacer-repeat sequence (e.g., a first spacer-repeat sequence linked at the 3' end to a second spacer-repeat sequence) and so on, to form, for example, a repeat-spacer-repeat-spacer-repeat with up to 10 spacer sequences alternating with up to 11 repeat sequences.

A crRNA of this invention can be "processed" or "unprocessed." An "unprocessed crRNA" may comprise at least one spacer linked at both the 5' end and at the 3' end to a full-length repeat sequence ("repeat-spacer-repeat" sequence). An unprocessed crRNA may comprise further spacer-repeat sequences linked to the 3' end of the repeat-spacer-repeat sequence (e.g., repeat-spacer-repeat-spacer-repeat-spacer-repeat-spacer-repeat and the like, up to about ten "spacer-repeat sequence" units). The design of a "processed crRNA may vary depending on whether the crRNA is intended for use with a Type I, Type II, or a Type III CRISPR-Cas system. Thus, in some embodiments, a "processed crRNA" may comprise a spacer sequence linked at its 5' end to the 3' end of a portion of consecutive nucleotides of a repeat sequence (e.g., "a handle"). In some embodiments, a processed crRNA may further comprise a full length repeat sequence or a portion of consecutive nucleotides of a repeat sequence, the full length repeat sequence or portion of a repeat sequence being linked at its 5' end to the 3' end of the spacer sequence.

A "spacer sequence" as used herein is a nucleotide sequence that is complementary to a target DNA The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA. Thus, in some embodiments, the spacer sequence can have one, two, three, four, or five mismatches as compared to the target DNA, which mismatches can be contiguous or noncontiguous. In some embodiments, the spacer sequence can have 70% identity to a target DNA. In other embodiments, the spacer nucleotide sequence can have 80% identity to a target DNA. In still other embodiments, the spacer nucleotide sequence can have 85%, 90%, 95%, 96%, 97%, 98%, 99% identity, and the like, to a target nucleotide sequence of a target gene. In representative embodiments, the spacer sequence has 100% complementarity to the target DNA. In particular embodiments, a spacer sequence has complete identity or substantial identity over a region of a target nucleotide sequence that is at least about 17 nucleotides to about 100 nucleotides in length or about 25 nucleotides to about 100 nucleotides in length.

In some embodiments, the 5' region of a spacer sequence can be identical to a target DNA while the 3' region of the spacer can be substantially identical to the target DNA and therefore the overall complementarity of the spacer sequence to the target DNA is less than 100%. Thus, for example, the first 7, 8, 9, 10, 11, 12, 13, 14, 15, 16, and the like, nucleotides in the 3' region of, for example, a 20 nucleotide spacer sequence (seed region) can be 100% complementary to the target DNA, while the remaining nucleotides in the 5' region of the spacer sequence are substantially complementary (e.g., at least about 70% complementary) to the target DNA. In some embodiments, the first 7 to 12 nucleotides of the 3' end of the spacer sequence can be 100% complementary to the target DNA, while the remaining nucleotides in the 5' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA. In some embodiments, the 3' end of the spacer sequence can be 75%-99% complementary to the target DNA, while the remaining nucleotides in the 5' region of the spacer sequence can be at least about 50% to about 99% complementary to the target DNA. In other embodiments, the first 7 to 10 nucleotides in the 3' end of the spacer sequence can be 75%-99% complementary to the target DNA, while the remaining nucleotides in the 5' region of the spacer sequence are at least about 50% to about 99% complementary to the target DNA. In other embodiments, the first 7 to 10 nucleotides in the 3' end of the spacer sequence can be 100% complementary to the target DNA, while the remaining nucleotides in the 5' region of the spacer sequence are substantially complementary (e.g., at least about 70% complementary) to the target DNA. In representative embodiments, the first 10 nucleotides (within the seed region) of the spacer sequence can be 100% complementary to the target DNA, while the remaining nucleotides in the 5' region of the spacer sequence are substantially complementary (e.g., at least about 70% complementary) to the target DNA. In an exemplary embodiment, the 5' region of a spacer sequence (e.g., the first 8 nucleotides at the 5' end, the first 10 nucleotides at the 5' end, the first 15 nucleotides at the 5' end, the first 20 nucleotides at the 5' end) can have about 75% identity or more (75% to about 100% identity) to a target DNA, while the remainder of the spacer sequence can have about 50% or more identity to the target DNA. Thus, for example, the first 8 nucleotides at the 5' end of a spacer sequence can be 100% identical to the target nucleotide sequence or it can have one or two mutations and therefore can be about 88% identical or about 75% identical to a target DNA, respectively, while the remainder of the spacer nucleotide sequence can be at least about 50% or more identical to the target DNA.

In some embodiments, a spacer sequence of this invention can be about 17 nucleotides to about 100 nucleotides in length. In representative embodiments, a spacer nucleotide sequence of this invention can be about 17 nucleotides to about 100 nucleotides in length for a crRNA (e.g., for a crRNA intended for use in a Type II CRISPR-Cas system) (e.g., about 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) or about 25 nucleotides to about 100 nucleotides in length for a crRNA (e.g., for a crRNA intended for use in a Type I or a Type III CRISPR-Cas system) (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein). In some particular embodiments, a spacer nucleotide sequence can be a length of about 17 to about 90 nucleotides, about 17 to about 80 nucleotides, about 17 to about 50 nucleotides, about 17 to about 40 nucleotides, about 17 to about 30 nucleotides, about 17 to about 25 nucleotides, about 17 to about 20 nucleotides, about 20 to about 50 nucleotides, about 20 to about 40 nucleotides, about 20 to about 30 nucleotides, about 20 to about 25 nucleotides, about 25 to about 90 nucleotides, about 25 to about 80 nucleotides, about 25 to about 50 nucleotides, about 25 to about 40 nucleotides, about 25 to about 35 nucleotides, about 25 to about 30 nucleotides, at least about 17 nucleotides, at least about 20 nucleotides, at least about 25 nucleotides, at least about 30 nucleotides, at least about 35 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides in length, or more, and any value or range therein.

In representative embodiments, a spacer sequence of a Type II CRISPR spacer-repeat nucleic acid of the invention comprises at least about 17 consecutive nucleotides of a target DNA or target nucleic acid, wherein at the 3' end of the spacer at least about 10 consecutive nucleotides of the at least about 17 consecutive nucleotides comprise at least about 90% complementarity to the target nucleic acid, wherein the target nucleic acid is adjacent to a protospacer adjacent motif (PAM) sequence in the genome of a bacterium or archaeon of interest. Moreover, in some embodiments, a spacer for a Type II CRISPR-Cas system can be extended at the 5' end with any nucleotide or nucleotide sequence because such an extension would fall outside of the part of the spacer sequence which Cas9 uses for binding target DNAs.

In other embodiments, a spacer sequence of a Type I CRISPR spacer-repeat nucleic acid of the invention comprises at least about 25 consecutive nucleotides of a target DNA or target nucleic acid, wherein at the 3' end of the spacer at least about 10 consecutive nucleotides of the at least about 25 consecutive nucleotides comprise at least about 90% complementarity to the target nucleic acid, wherein the target nucleic acid is adjacent to a protospacer adjacent motif (PAM) sequence in the genome of a bacterium or archaeon of interest.

In further embodiments, a spacer sequence of a Type III CRISPR spacer-repeat nucleic acid of the invention comprises at least about 25 consecutive nucleotides of a target DNA or target nucleic acid, wherein at the 3' end of the spacer at least about 10 consecutive nucleotides of the at least about 25 consecutive nucleotides comprise at least about 90% complementarity to the target nucleic acid, wherein the target nucleic acid is adjacent to a sequence having complementarity of 50% or less (e.g., 50%, 45%, 40%, 35%, 30%, 25%, 20%, 15%, 10%, 5%, and the like and any range or value therein) to the 5' handle of the crRNA in the genome of a bacterium or archaeon of interest.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

A "trans-activating CRISPR (tracr) nucleic acid" or "tracr nucleic acid" as used herein refers to any tracr RNA (or its encoding DNA). A tracr nucleic acid comprises from 5' to 3' a bulge, a *nexus* hairpin and terminal hairpins, and optionally, at the 5' end, an upper stem (See, Briner et al. (2014) *Molecular Cell.* 56(2):333-339). A tracr nucleic acid functions in hybridizing to the repeat portion of mature or immature crRNAs, recruits Cas9 protein to the target site, and may facilitate the catalytic activity of Cas9 by inducing structural rearrangement. Sequences for tracrRNAs are specific to the CRISPR-Cas Type II system and can be variable. Any tracr nucleic acid, known or later identified, can be used with this invention. In some embodiments, a tracr nucleic acid can be fused to a crRNA of the invention to form a single guide nucleic acid, and therefore, in some embodiments, an antimicrobial (chimeric construct) of the invention comprises a CPP linked to a crRNA and a tracr nucleic acid. In an exemplary embodiment, a Type II crRNA may further comprises a trans-activating CRISPR (tracr) sequence to form a single guide RNA (sgRNA), the single guide RNA having a 3' end and 5' end and comprising: (A) a spacer sequence having a 5' end and a 3' end and a length of about 17-100 nucleotides, (B) a Type II repeat sequence having a 5' end and a 3' end, (C) a loop having a 5' end and a 3' end; and (D) a trans-activating CRISPR (tracr) sequence having a 5' end and a 3' end, wherein the spacer sequence is linked at the 3' end to the 5' end of the Type II repeat sequence, the 3' end of the Type II repeat sequence is linked to the 5' end of the loop, and the 3' end of the loop is linked to the 5' end of the tracr sequence. In some embodiments, the loop (e.g., linker) may comprise one to about 100 nucleotides.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 70%, at least about 75%, at least about 80%, at least about 85%, at least about 90%, at least about 95, 96, 96, 97, 98, or 99% identity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin and Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

As used herein, a "target DNA," "target nucleotide sequence," "target region," or a "target region in the genome" refers to a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a crRNA of this invention. In some embodiments, a target region may be about 17 to about 100 consecutive nucleotides in length (e.g., about 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) or about 25 to about 100 consecutive nucleotides in length (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) which in Type I and Type II CRISPR-Cas systems is located immediately 3' or 5' to a PAM sequence, respectively, in the genome of the organism.

A target nucleotide sequence or target DNA in a Type I and Type II system is located adjacent to or flanked by a PAM (protospacer adjacent motif). While PAMs are often specific to the particular Type I or Type II CRISPR-Cas system, a PAM sequence can be determined by those skilled in the art through established experimental and computational approaches. Thus, for example, experimental approaches include targeting a sequence flanked by all possible nucleotides sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, a target DNA can be from a bacterial genome, bacterial plasmid and/or lysogenic phage genome in the cell of a target bacterium. In other embodiments, a target DNA can be from an archaeon genome, archaeon plasmid and/or archaeon-infecting virus in the cell of a target archaeon. In representative embodiments, the target DNA is unique to a bacterial strain, species, or genera or an archaeal strain, species, or genera.

A "target bacterium" or "target bacterial cell" as used herein includes any genera, species or strain of bacteria having an endogenous Type I, Type II, or Type III CRISPR-Cas system. The term "target bacterium" or "target bacterial cell" also includes any genera, species or strain of bacteria into which a heterologous Type I, Type II, or Type III CRISPR-Cas system has been introduced. A "target archaeon" or "target archaeal cell" as used herein includes any genera, species or strain of archaea having an endogenous Type I and/or Type III CRISPR-Cas system. The term "target archaeon" or "target archaeal cell" as used herein also refers to any genera, species or strain of archaea into which a heterologous Type I, Type II, or Type III CRISPR-Cas system has been introduced. Thus, in some embodiments, a target bacterial cell or target archaeal cell useful with this invention does not express an endogenous CRISPR-Cas system but, as is well-known to a person skilled in the art of CRISPR technology, bacteria and archaea can be readily transformed to express components of a heterologous CRISPR-Cas system. The selection of the introduced CRISPR-Cas system (e. g., Type I, Type II, or Type III) is based on the crRNA of the crRNA-CPP construct of the invention. Thus, if the crRNA is a Type I-E crRNA (e.g., comprises a Type I-E repeat) then the CRISPR-Cas system that is selected for introduction into the target bacterium or target archaeon is a Type I-E CRISPR-Cas system as well. The components of Type I, Type II, and Type III CRIPSR systems are well known (Gomaa et al. *mBio* 5(1): e00928-13 (2014); Semenova et al. *Nucleic Acids Res.* 43(12):6049-61 (2015); Selle et al. *Proc Natl Acad Sci USA.*;112(26):8076-81 (2015); Marraffini et al. *Science* 322 (5909): 1843-1845 (2008); and Hale et al. *Mol. Cell.* 54(3): 292-302 (2012)).

Thus, for example, a target bacterial cell or archaeal cell may be transformed with a Type I CRISPR-Cas system to express the Cascade polypeptides and at least one Cas3 polypeptide. For a Type II CRISPR-Cas system, the target bacterium or target archaeon may be transformed with a trans-activating CRISPR (tracr) sequence and a polynucleotide encoding a Cas9 polypeptide. Alternatively, if the chimeric construct of the invention comprises an sgRNA, then only a polynucleotide encoding a Cas9 polypeptide needs to be introduced into a target bacterium or target archaeon. For a Type III CRISPR-Cas system, the target bacterium or archaeon may be transformed with one or more nucleic acid constructs encoding Cas polypeptides, Csm polypeptides and/or Cmr polypeptides. Accordingly, any bacterium or archaeon transformed with a CRISPR Type I, Type II or Type III system may be a target bacterium or target archaeon. The chimeric construct can then be contacted with the cell to drive plasmid removal, lysogenic bacteriophage removal, or genome editing. For genome editing, the bacterium may be genetically manipulated prior to contact with the chimeric construct. The manipulation may be performed by introducing a DNA template for homologous recombination and an expressed recombinase as needed. The crRNA may then be designed to target the original genomic sequence but not the recombined sequence.

Exemplary target bacteria or target archaea having at least one endogenous CRISPR-Cas system that may be useful with this invention include, but are not limited to, *Acinetobacter baumannii, Campylobacter jejuni, Clostridium difficile, Escherichia coli, Francisella tularensis, Mycobacterium tuberculosis, Novicida meningitidis, Pectobacterium atrosepticum, Pseudomonas aeruginosa, Salmonella enterica, Klebsiella pneumoniae, Staphylococcus aureus, Streptococcus pyogenes,* or *Streptococcus thermophilus.*

Any polynucleotide of this invention (e.g., a heterologous polynucleotide encoding a Cas polypeptide (e.g., Cas9, Cas3, Cas7, etc.), a Cascade polypeptide, a Csm polypeptide and/or a Cmr polypeptide) can be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species-specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original nucleotide sequence. Thus, in representative embodiments of the invention, a polynucleotide of this invention can be codon optimized for expression in the particular organism/species of interest.

In some embodiments, the polynucleotides and polypeptides of the invention are "isolated." An "isolated" polynucleotide or an "isolated" polypeptide is a nucleotide sequence or polypeptide sequence that, by the hand of man, exists apart from its native environment and is therefore not a product of nature. An isolated polynucleotide or polypeptide may exist in a purified form that is at least partially separated from at least some of the other components of the naturally occurring organism or virus, for example, the cell or viral structural components or other polypeptides or polynucleotides commonly found associated with the polypeptide or polynucleotide. In representative embodiments, the isolated polynucleotide and/or the isolated polypeptide is at least about 1%, 5%, 10%, 20%, 30%, 40%, 50%, 60%, 70%, 80%, 90%, 95%, or more pure.

In other embodiments, an isolated polynucleotide or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, by the hand of man, they exist apart from their native environment and therefore are not products of nature, however, in some embodiments, they can be introduced into and exist in a recombinant host cell.

In further embodiments of the invention, polynucleotides comprising tracr nucleic acids and/or crRNA or, and polynucleotides encoding a Cas polypeptides, Cascade polypeptides, Csm polypeptides, Cmr polypeptides, and the like, can be operatively associated with a variety of promoters, terminators and other regulatory elements for expression in various organisms or cells. Thus, in representative embodiments, at least one promoter and/or terminator can be operably linked to a polynucleotide of the invention. Any promoter useful with this invention can be used and includes, for example, promoters functional with the organism of interest including but not limited to constitutive, inducible, developmentally regulated, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of the nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase and directs the initiation of transcription. In general, promoters are found 5', or upstream, relative to the start of the coding region of the corresponding coding sequence. The promoter region may comprise other elements that act as regulators of gene expression. These include, but are not limited to, a −35 element consensus sequence and a −10 consensus sequence (Simpson. 1979. *Proc. Natl. Acad. Sci. U.S.A.* 76:3233-3237).

Promoters can include, for example, constitutive, inducible, temporally regulated, developmentally regulated, chemically regulated promoters for use in the preparation of recombinant nucleic acid constructs, polynucleotides, expression cassettes and vectors comprising the polynucleotides and recombinant nucleic acid constructs of the invention. These various types of promoters are known in the art.

Thus, in some embodiments, expression of a construct of the invention can be made constitutive, inducible, temporally regulated, developmentally regulated, chemically regulated promoters using the recombinant nucleic acid constructs of the invention operatively linked to the appropriate promoter functional in an organism of interest. In representative embodiments, repression can be made reversible using the recombinant nucleic acid constructs of the invention operatively linked to, for example, an inducible promoter functional in an organism of interest.

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Exemplary promoters include useful with this invention include promoters functional in bacteria. A promoter useful with bacteria can include, but is not limited to, L-arabinose inducible (araBAD, $P_{BAD}$) promoter, any lac promoter, L-rhamnose inducible (rhaP$_{BAD}$) promoter, T7 RNA polymerase promoter, trc promoter, tac promoter, lambda phage promoter ($p_L$, $p_L$-9G-50), anhydrotetracycline-inducible (tetA) promoter, trp, lpp, phoA, recA, pro U, cst-1, cadA, nar, lpp-lac, cspA, T7-lac operator, T3-lac operator, T4 gene 32, T5-lac operator, nprM-lac operator, Vhb, Protein A, corynebacterial-*E. coli* like promoters, thr, horn, diphtheria toxin promoter, sig A, sig B, nusG, SoxS, katb, α-amylase (Parry), Ptms, P43 (comprised of two overlapping RNA polymerase σ factor recognition sites, σA, σB), Ptms, P43, rplK-rplA, ferredoxin promoter, and/or xylose promoter. (See, K. Terpe *Appl. Microbiol, Biotechnol.* 72:211-222

(2006); Hannig et al. Trends in Biotechnology 16:54-60 (1998); and Srivastava Protein Expr Purif 40:221-229 (2005)).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the RNAs and/or the polypeptides of the invention to be synthesized only when, for example, an organism is treated with the inducing chemicals. Depending upon the objective, the promoter may be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya et al. 2005. *Nature* 438:441-442).

In some embodiments, a nucleic acid comprising components of a heterologous CRISPR-Cas system can be an "expression cassette" or can be comprised within an expression cassette. As used herein, "expression cassette" means a recombinant nucleic acid construct comprising one or more polynucleotides of the invention, wherein the recombinant nucleic acid construct is operably associated with at least one control sequence (e.g., a promoter). Thus, some aspects of the invention provide expression cassettes designed to express the polynucleotides of the invention.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). In some embodiments of this invention, terminators can be operably linked to a recombinant nucleic acid.

An expression cassette also can include a nucleotide sequence encoding a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or whether the marker is simply a trait that one can identify through observation or testing, such as by screening (e.g., fluorescence). Of course, many examples of suitable selectable markers are known in the art and can be used in the expression cassettes described herein.

In addition to expression cassettes, the recombinant polynucleotides described herein (e.g., polynucleotides comprising a tracr nucleic acid, and polynucleotides encoding Cas polypeptides, Cascade polypeptides, Csm polypeptides, Cmr polypeptides, and the like) can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a prokaryotic host either by integration into the cellular genome or exist extrachromosomally (e.g. autonomous replicating plasmid with an origin of replication).

Additionally included are shuttle vectors by which is meant a DNA vehicle capable, naturally or by design, of replication in two different host organisms, such as broad-host plasmids or shuttle vectors with multiple origins-of-replication. In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, a polynucleotide of this invention and/or expression cassettes comprising polynucleotides of this invention can be comprised in vectors as described herein and as known in the art.

"Introducing," "introduce," "introduced" (and grammatical variations thereof) in the context of a polynucleotide of interest means presenting a polynucleotide of interest to a host organism or a cell of the organism (e.g., host cell such as a bacterial cell) in such a manner that the polynucleotide gains access to the interior of a cell and includes such terms as "transformation," "transfection," and/or "transduction." Where more than one polynucleotide is to be introduced these polynucleotides can be assembled as part of a single polynucleotide or nucleic acid construct, or as separate polynucleotide or nucleic acid constructs, and can be located on the same or different expression constructs or transformation vectors.

The terms "transformation," "transfection," and "transduction" as used herein refer to the introduction of a heterologous polynucleotide into a cell (e.g., polynucleotides of heterologous CRISPR-Cas systems). Such introduction into a cell may be stable or transient. Thus, in some embodiments, a host cell or host organism is stably transformed with a nucleic acid molecule of the invention. In other embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell and cannot be maintained through antibiotic selection or addictive systems.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plasmid genome, and therefore includes integration of the nucleic acid construct into, for example, the plasmid genome. Stable transformation as used herein can also refer to a transgene that is maintained extrachromosomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a bacterium). Stable transformation of a cell can be detected by, for example, a Northern blot hybridization assay of RNA of the cell with nucleic acid sequences which specifically hybridize with a nucleotide sequence of a transgene introduced into the cell. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

A polynucleotide of the invention can be introduced into a cell by any method known to those of skill in the art. Exemplary methods of transformation include transformation via electroporation of competent cells, passive uptake by competent cells, chemical transformation of competent cells, as well as any other electrical, chemical, physical (mechanical) and/or biological mechanism that results in the introduction of nucleic acid into a cell, including any combination thereof.

In some aspects, transformation of a cell may comprise nuclear transformation. In other aspects, transformation of a cell may comprise plasmid transformation and conjugation.

Procedures for transforming prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence, for example, nucleotide sequences comprising the CRISPR nucleic acids and encoding the CRISPR polypeptides, can therefore be introduced into a host cell in any number of ways that are well known in the art to generate a bacterium or archaeon comprising, for example, a heterologous CRISPR-Cas system. The methods of the invention do not depend on a particular method for introducing one or more nucleotide sequences into an organism, only that they gain access to the interior of the cell. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events.

"Effective amount" as used herein refers to an amount of a chimeric construct and/or composition of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of skill in the art by reference to the pertinent texts and literature and/or by using routine experimentation. In some embodiments, an effective amount of a chimeric construct of the invention or composition thereof may be about 1 nM to 10 uM. In some embodiments, an effective amount may be an amount that reduces the bacterial or archaeal cell load by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject. In some embodiments, a therapeutically effective amount of a chimeric construct of the invention or composition thereof may be about 1 nM to 10 uM. In some embodiments, a therapeutically effective amount may be an amount that reduces the bacterial or archaeal cell load by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

By the terms "treat," "treating," or "treatment," it is intended that the severity of the subject's condition is reduced or at least partially improved or modified and that some alleviation, mitigation or decrease in at least one clinical symptom is achieved, and/or there is a delay in the progression of the disease or condition, and/or delay of the onset of a disease or illness. With respect to an infection, a disease or a condition, the term refers to, e.g., a decrease in the symptoms or other manifestations of the infection, disease or condition. In some embodiments, treatment provides a reduction in symptoms or other manifestations of the infection, disease or condition by at least about 5%, e.g., about 10%, 15%, 20%, 25%, 30%, 35%, 40%, 45%, 50% or more.

Further, with respect to an infection, a disease or a condition, the terms "treat," "treating," or "treatment of" and the like refer to, e.g., elimination of or a decrease in the presence or amount of a microorganism (e.g., bacteria) in the subject. Thus, by treating the infection, disease, and/or condition in the subject, the infection, disease, and/or condition is ameliorated, alleviated, severity reduced, symptoms reduced and the like as compared to a similar subject not treated with the chimeric constructs of this invention, thereby treating the infection, disease and/or condition. In some embodiments, the treatment of an infection by a bacterium as described herein can be, for example, bactericidal and/or bacteriostatic. Thus, in some embodiments, the presence of a bacterium may be reduced by about 10% to about 100% (e.g., 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, or any value or range therein) upon contact with the chimeric construct of the invention of a composition thereof.

The term "bactericidal," refers to killing the microorganism and the term "bacteriostatic" "refers to inhibiting or retarding the growth of a microorganism (e.g., bacteria or archaea), without killing the microorganism.

As used herein, the terms "eliminate," "eliminated," and/or "eliminating" refer to complete cessation of the specified activity.

As used herein, the terms "retarding the growth" or "retardation of growth" refers to reducing, delaying, inhibiting, and/or hindering the activity contributing to the growth and multiplication of a microorganism.

In some embodiments, a subject in need of treatment may be identified by, for example, well-established hallmarks of an infection, such as fever, puls, culture of organisms, and the like, or a subject may be treated prior to infection to prevent or reduce the likelihood of infection in the subject.

The terms "prevent," "preventing," and "prevention" (and grammatical variations thereof) refer to prevention and/or delay of the onset of an infection, disease, condition and/or a clinical symptom(s) in a subject and/or a reduction in the severity of the onset of the infection, disease, condition and/or clinical symptom(s) relative to what would occur in the absence of carrying out the methods of the invention prior to the onset of the disease, disorder and/or clinical symptom(s). Thus, for example, to prevent infection in a hospital setting, food, surfaces, medical tools and devices may be treated with the chimeric constructs or compositions thereof.

A "prevention effective" amount as used herein is an amount of a chimeric construct of the invention that is sufficient to reduce a bacterial or archaeal load by at least about 10% to about 100%, and any range or value therein.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The present invention finds use in veterinary and medical applications as well as research applications. A "subject" of the invention includes any animal that has or is susceptible to an infection, disease or condition involving bacteria and/or archaea. Thus, such subject can be mammals, avians, reptiles, amphibians, or fish. Mammalian subjects include but are not limited to humans, non-human primates (e.g., gorilla, monkey, baboon, and chimpanzee, etc.), dogs, cats, goats, horses, pigs, cattle, sheep, and the like, and laboratory animals (e.g., rats, guinea pigs, mice, gerbils, hamsters, and the like). Avian subjects include but are not limited to chickens, ducks, turkeys, geese, quail, pheasants, and birds kept as pets (e.g., parakeets, parrots, macaws, cockatoos, *canaries*, and the like). Suitable subjects include both males and females and subjects of any age, including embryonic (e.g., in utero or in ovo), infant, juvenile, adolescent, adult and geriatric subjects. In some embodiments, a subject of this invention is a human.

A "subject in need" of the methods of the invention can be a subject known to have, suspected of having, or having an increased risk of developing an infection, disease, or condition, including secondary infections, caused by, for example, bacteria or archaea.

In some embodiments, the subject is one that has a bacterial infection, has had a bacterial infection, or is at risk for a bacterial infection. A subject at risk for a bacterial infection can be one that is, for example, in a hospital and is thereby exposed to infectious bacteria.

As a further aspect, the invention provides pharmaceutical compositions and methods of administering the same to treat bacterial and/or archaeal infections. The pharmaceutical composition may comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The compositions of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science And Practice of Pharmacy* ($21^{th}$ Ed. 2005). In the manufacture of a pharmaceutical composition according to the invention, the compound (including the physiologically acceptable salts thereof) is typically admixed with, inter alia, an acceptable carrier. The carrier can be a solid (including a powder) or a liquid, or both, and is preferably formulated with the compound as a unit-dose composition, for example, a tablet, which can contain from 0.01 or 0.5% to 95% or 99% by weight of the compound. One or more compounds can be incorporated in the compositions of the invention, which can be prepared by any of the well-known techniques of pharmacy.

A further aspect of the invention is a method of treating subjects in vivo, comprising administering to a subject a pharmaceutical composition comprising a compound of the invention in a pharmaceutically acceptable carrier, wherein the pharmaceutical composition is administered in a therapeutically effective amount. Administration of the compounds of the present invention to a human subject or an animal in need thereof can be by any means known in the art for administering compounds.

The chimeric constructs of the invention and compositions thereof include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). In some embodiments, the composition is delivered to the site of tissue infection. The most suitable route in any given case will depend on the nature and severity of the condition being treated and on the nature of the particular compound which is being used.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the compound, which preparations are preferably isotonic with the blood of the intended recipient. These preparations can contain antioxidants, buffers, bacteriostats and solutes which render the composition isotonic with the blood of the intended recipient. Aqueous and non-aqueous sterile suspensions can include suspending agents and thickening agents. The compositions can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Compositions suitable for rectal administration are preferably presented as unit dose suppositories. These can be prepared by admixing the compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Compositions suitable for transdermal administration can be presented as discrete patches adapted to remain in intimate contact with the epidermis of the recipient for a prolonged period of time. Compositions suitable for transdermal administration can also be delivered by iontophoresis (see, for example, Tyle, *Pharm. Res.* 3:318 (1986)) and typically take the form of an optionally buffered aqueous solution of the compound. Suitable compositions comprise citrate or bis\tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton and Jones, *Drug Delivery to the Respiratory Tract*, Ellis Horwood (1987); Gonda (1990) *Critical Reviews in Therapeutic Drug Carrier Systems* 6:273-313; and Raeburn et al., *J Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release composition.

Further, the present invention provides liposomal formulations of the compounds disclosed herein. The technology for forming liposomal suspensions is well known in the art. When the compound is in the form of an aqueous-soluble material, using conventional liposome technology, the same can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. When the compound of interest is water-insoluble, again employing conventional liposome formation technology, the compound can be substantially entrained within the hydrophobic lipid bilayer which forms the structure of the liposome. In either instance, the liposomes which are produced can be reduced in size, as through the use of standard sonication and homogenization techniques. The liposomal compositions containing the compound disclosed herein, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In addition to compound, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the composition is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

In particular embodiments, the compound is administered to the subject in a therapeutically effective amount, as that term is defined above. Dosages of pharmaceutically active compounds can be determined by methods known in the art, see, e.g., Remington, *The Science And Practice of Pharmacy* (21$^{th}$ Ed. 2005). The therapeutically effective dosage of any specific compound will vary somewhat from compound to compound, and patient to patient, and will depend upon the condition of the patient and the route of delivery. In one embodiment, the compound is administered at a dose of about 0.001 to about 10 mg/kg body weight, e.g., about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, or 10 mg/kg. In some instances, the dose can be even lower, e.g., as low as 0.0005 or 0.0001 mg/kg or lower. In some instances, the dose can be even higher, e.g., as high as 20, 50, 100, 500, or 1000 mg/kg or higher. The present invention encompasses every sub-range within the cited ranges and amounts.

The inventors have developed new antimicrobial compositions comprising chimeric constructs between CRISPR (Clustered Regularly Interspaced Short Palindromic Repeats) RNAs (crRNAs) and cell-penetrating peptides (CPPs) for delivery to target cells, including, but not limited to, mammalian cells, bacterial cells and/or archaeal cells. Thus, CPPs are fused to crRNAs to guide an endogenous or heterologous CRISPR-Cas system present in a bacterium or archaeon. The system is directed to cleave specified sequences, whether to kill a target cell, remove endogenous plasmids or lysogenic bacteriophages from a bacterium or archaeon or "drive genome editing" in a target cell, such as a mammalian cell, bacterial cell and/or archaeal cell. Genome editing is accomplished by either guiding the DNA repair pathways to fix the cleavage with a defined sequence or to perform recombineering before administering the chimeric construct, the construct would this kill any cells that did not undergo editing. The chimeric constructs of the invention (CPP-crRNA fusions) can be used, for example, in the pharmaceutical and agricultural industries to clear bacterial infections and in the biotechnology industry for the manipulation of bacterial strains and communities.

Cell penetrating peptides (CPPs) are small peptide sequences of about 10 amino acids that can transport across the cell wall and cell membrane (see, e.g., Fischer et al. *ChemBioChem* 6:2126-2142 (2005)). While CPPs have primarily been developed for the delivery of small-molecule drugs, proteins, and nucleic acids to mammalian cells, a number of CPPs have been explored in bacteria. These CPPs were originally used to sensitize cells to antibiotics (Vaara, et al. *Antimicrob. Agents Chemother.* 40, 1801-1805 (1996)), although follow-up work demonstrated that fusing CPPs to antisense nucleic acids based on peptide nucleic acids (PNAs) or on phosphorodiamidate morpholino oligomers (PMOs) could silence target mRNAs (Ghosal et al. *Nucleic Acid Ther.* 22, 323-334 (2012); Mellbye et al. *Antimicrob. Agents Chemother.* 53, 525-530 (2009); Mellbye et al. *J. Antimicrob. Chemother.* 65, 98-106 (2010); Greenberg et al. *J. Infect. Dis.* 201, 1822-1830 (2010); Good et al. *Nat. Biotechnol.* 19, 360-364 (2001)). Targeting mRNAs encoding essential proteins has led to sequence-specific bactericidal and bacteriostatic effects. Numerous CPP sequences have been reported and many allow delivery across a broad swath of gram-positive and/or gram-negative bacteria (Vaara, et al. *Antimicrob. Agents Chemother.* 40, 1801-1805 (1996)), as well as mammalian cells.

Despite advances in using CPPs and antisense RNAs as antimicrobials, this platform is plagued by a number of major issues. First, high concentrations (1-10 μM) of the CPP fusions are required for activity owing to the stoichiometric nature of mRNA binding—potentially leading to toxicity in animals (Good et al. *Nat. Biotechnol.* 19, 360-364 (2001)). Furthermore, identifying a target sequence within an essential gene that is unique to a given genera, species, or strain would be challenging at best. Finally, killing a bacterial cell through this approach likely requires a sustained supply of the CPP fusion, as cells would be expected to recover from transient silencing.

The present invention overcomes these challenges by coupling CPPs with an entirely different nucleic acid-based strategy: CRISPR RNAs (crRNAS). crRNAs are encoded within long arrays of identical repeats and intervening spacers, where the arrays undergo processing to form individual CRISPR RNAs. To date, CRISPR-Cas systems have been found in about 40% of bacteria and come in three general groups (Types I, II, III) based on the Cas proteins associated with each system (Makarova et al. *Nat. Rev. Microbiol.* 9, 467-477 (2011)). In embodiments of the invention, CPPs can be covalently or non-covalently linked to the processed or unprocessed form of the crRNA. crRNAs contacted with a target bacteria or archaea would then associate with an endogenous CRISPR-Cas system or a heterologous CRISPR-Cas system that is introduced into the target bacteria or archaea, thereby guiding the CRISPR-Cas system to bind, cleave, and degrade targeted DNA sequences. In some embodiments, mammalian cells comprising a heterologous CRISPR-Cas system can be targeted using the chimeric constructs of the invention. Because CRISPR irreversibly destroys target DNA, as little as a single molecule of a CPP-crRNA fusion would be expected to induce targeted killing. Furthermore, because the CRISPR-Cas system must be active and compatible with the CRISPR RNA, this approach is expected to confer a level of unparalleled specificity.

In some embodiments, a CRISPR-Cas system in a target bacterium is first identified and the PAM elucidated (for Type I, Type II systems). The PAM can be determined using establishing approaches, including bioinformatics prediction or high-throughput screening (Patanayak et al. 2013. *Nat. Biotechnol.* 31:839-843) or the transformation of target plasmid DNA (Esvelt et al. 2013. *Nat. Methods* 10:1116-1121; Jiang et al. 2013. *Nat. Biotechnol.* 31:233-239)). Once the PAM is determined, bioinformatics-based comparisons can be used to identify sequences unique to the target strain, species, or genera. This sequence can then be integrated into the crRNA as the spacer. For Type III systems, target recognition is determined by mismatches between the 5' handle and the sequence flanking the target.

The crRNA can be designed using an unprocessed form or a processed form. In some embodiments, an unprocessed form comprises a repeat-spacer-repeat sequence. The leading repeat sequence is cleaved off, while the terminal repeat sequence is cleaved and retained with the spacer as part of Cascade (Type I), Cas9 (Type II), or the Cmr/Csm complex (Type III). In some embodiments, an unprocessed Type I crRNA, Type II crRNA or Type III crRNA may comprise up to nine additional consecutive spacer-repeat sequences, each having a 5' end and a 3' end and each linked at the 3' end to the 5' end of the next-spacer-repeat sequence Once designed and synthesized (either chemically or via in vitro transcription), the crRNA can be joined to a CPP via, for example, a non-covalent association (based on the anionic RNA binding to the cationic CPP) or via a covalent bond. The processed version of a Type I and III crRNA can only be covalently bonded to a CPP at their 3' end, whereas all others may be covalently bonded at the 5' end, 3' end, or both. FIG. 1 provides examples of various configurations of CPP-crRNA conjugates. Methods for conjugating CPPs and various nucleic acids (and derivatives thereof) are well established (see, e.g., Zatsepin et al. *Curr. Pharm. Des.* 11, 3639-3654 (2005)).

The CPP-crRNA chimeric constructs may be used in a wide variety of applications. For example, they may be used to kill a target cell (e.g., a mammalian cell, a bacterial cell, an archaeal cell) in a sequence specific manner, as sequence-specific antimicrobials, in genome editing, and for the curing of plasmids or lysogenic bacteriophages. As sequence-specific antimicrobials, the crRNA may guide genome targeting, leading to bacterial or archaeal cell death. For genome editing, the bacterial or archaeal cells utilize a repair template and, in some embodiments, a heterologous repair pathway. The repair template may mutate the target site or PAM, thereby preventing killing by the CRISPR-Cas system. However, any bacteria that have not been so mutated can be eliminated from the population by the chimeric CPP-crRNA constructs of the invention. Finally, for plasmid and bacteriophage curing, the crRNA may be designed to target a resident plasmid or bacteriophage—whether naturally present or introduced into the cell, thereby resulting in the plasmid being cleaved and removed.

When using this technology as an antimicrobial, a bacterium or archaeon may comprise an endogenous CRISPR-Cas system or it may comprise an introduced heterologous CRISPR-Cas system. While the fraction of bacteria with active CRISPR-Cas systems is likely well below 40%, there are a few exemplary species of clinical relevance having endogenous systems that may be targeted using the chimeric constructs of the invention provided in Table 1.

TABLE 1

| Clinically relevant bacterial species. | |
|---|---|
| Bacterium | CRISPR System |
| Acinetobacter baumannii | Type I |
| Clostridium difficile | Type I-C |
| Escherichia coli | Type I-E, I-F |
| Francisella tularensis | Type II-A |
| Mycobacterium tuberculosis | Type I, III |
| Novicida meningitidis | Type II-C |
| Pseudomonas aeruginosa | Type I-F |
| Staphylococcus aureus | Type II-A |
| Streptococcus pyogenes | Type II-A |

Accordingly, in one embodiment, a chimeric construct comprising, consisting essentially of, or consisting of a cell penetrating peptide (CPP) linked to a CRISPR RNA (crRNA) is provided. In some embodiments, the CPP can be covalently linked to the crRNA. In other embodiments, the CPP can be noncovalently linked to the crRNA as described herein.

Any CPP that can transport across the cell wall and cell membrane may be useful for linking with a crRNA of the present invention as described herein. Exemplary CPPs useful with this invention include cationic peptides (e.g., TAT and TAT-derived peptides, nuclear localization sequences, poly-arginine peptides, synB1); Beta-peptides; chimeric CPPs (e.g., Chariot, MPG, Transportan, Loligomers); hydrophobic CPPs (e.g., membrane permeable sequences, fusion sequence of HIV-gp41); PreS2-TLM CPPs; calcitonin-derived peptides; proline rich CPPs (e.g., proline-rich dendrimers, N-terminal repetitive domain of maize gamma-zein); amphipathic peptides (e.g., penetratin and penetratin derived peptides, retro-inverso, W/R penetration); and/or antimicrobial peptides and/or CPP derived from antimicrobial peptides (e.g., buforin, magainin); pVEC; and/or Tp10) (see, e.g., Fischer et al. *ChemBioChem* 6:2126-2142 (2005)).

Exemplary CPPs useful with the invention are provided in Table 2.

TABLE 2

A selection of CPPs used in bacteria.
X is 6-aminocaproic acid, B is β-alanine, Ahx is 6-aminohexanoic acid.

| Peptide | Bacterium | Reference |
|---|---|---|
| (KFF)₃K | E. coli, S. aureus, M. smegmatis | Good et al. Nat. Biotechnol. 19, 360-364 (2001); Nekhotiaeva et al. Mol. Ther. J. Am. Soc. Gene Ther. 10, 652-659 (2004); Kulyté et al. J. Mol. Microbiol. Biotechnol. 9, 101-109 (2005) |
| (RXR)₄B | S. aureus | Liang et al. Int. J. Infect. Dis. IJID Off Publ. Int. Soc. Infect. Dis. 30, 1-6 (2015) |
| PKKKRKV | M. smegmatis | Kulyté et al. J. Mol. Microbiol. Biotechnol. 9, 101-109 (2005) |
| (RAhxR)₄B | P. aeruginosa | Ghosal et al. Nucleic Acid Ther. 22, 323-334 (2012). |

Thus, in exemplary embodiments, the CPP of the chimeric construct of the invention may comprise, consist essentially of, or consist of (KFF)₃K (SEQ ID NO:1), (RXR)₄B (SEQ ID NO:2), PKKKRKV (SEQ ID NO:3), (RAhxR)₄B (SEQ ID NO:4), wherein X is 6-aminocaproic acid, B is b-alanine and Ahx is 6-aminohexanoic acid.

In further exemplary embodiments, the CPP of the chimeric construct of the invention may comprise, consist essentially of, or consist of a penetration CPP (e.g., RQIKIWFQNRRMKWKK, SEQ ID NO:5), a Tat peptide (ex: RKKRRQRRR, SEQ ID NO:6), a calcitonin-derived CPP (e.g., LGTYTQDFNKFHTFPQTAIGVGAP, SEQ ID NO:7), a nuclear localization sequence (e.g., VQRKRQKLMP (SEQ ID NO:8), SKKKKTKV (SEQ ID NO:9), GRKRKKRT (SEQ ID NO:10)), a polybasic CPP (e.g., RRRERRAEK (SEQ ID NO:11), KCPSRRPKR (SEQ ID NO:12)), an
N-terminal repetitive domain of maize gamma-zein CPP (e.g., (VRLPPP)n(VHLPPP)n(VKLPPP)n, SEQ ID NO:13), a peptide from gp41 fusion sequence (e.g., AVGAIGALFLGFLGAAG, SEQ ID NO:14), a preS2-TLM (e.g., PLSSIFSRIGDP, SEQ ID NO:15), a signal-sequence hydrophobic region (SSHR) (e.g., AAVALLPAVLLALLAP, SEQ ID NO:16), a SSHR (e.g., VTVLALGALAGVGVG, SEQ ID NO:17); a pVEC (e.g., IAARIKLRSRQHIKLRHL, SEQ ID NO:18); a Vpr (e.g., DTWPGVEALIRILQQLLFIH FRIGCQH, SEQ ID NO:19); a CPP from pestivirus envelope glycoprotein (e.g., RQGAARVTSWLGRQLRIAGKRLEGRSK, SEQ ID NO:20); aCPP derived from the prion protein (e.g., MANLGYWLLALFVTMWTDVGLC KKRPKP, SEQ ID NO:21); an antimicrobial peptide or a CPP derived from antimicrobial peptides (e.g., buforin (TRSSRAGLQWPVGRVHRLLRK, SEQ ID NO:22), magainin (GIGKFLHSAKKWGKAFVGQIMNS, SEQ ID NO:23), or LL-37 (LLGDFFRKSKEKIGKEFKRIVQRIKDFLRNLVPRTES, SEQ ID NO:24)); a SynB peptide (e.g., RGGRLSYSRRRFSTSTGR (SEQ ID NO:25), RRLSYSRRRF (SEQ ID NO:26)); a S4₁₃, S4₁₃-13 (e.g., ALWKTLLKKVLKA ALWKTLLKKVLKAPKKKRKV, SEQ ID NO:27); a proline-rich CPPs (e.g., PRPLPFPRPG, SEQ ID NO:28); a transportan (e.g., GWTLNSAGYLLGKINLKALAALAKKIL, SEQ ID NO:29); a polyarginine (CPPs (RRRRRRRR (R₈), SEQ ID NO:30); a
KLA peptide/model amphipathic peptide (MAP) (e.g., KLALKLALKALKAALKLA, SEQ ID NO:31); a modeled Tat peptide (e.g., YARAAARQARA, SEQ ID NO:32); a β-sheet-forming peptide (e.g., DPKGDPPKGVTVTVTVTVTG KGDPKPD, SEQ ID NO:33); a retro-inverso forms of established CPP (e.g., KKWKMRRNQFWVRVQR, SEQ ID NO:34); a W/R penetratin (e.g., RRWRRWWWRRWWRRWRR, SEQ ID NO:35); a MPG (e.g., GALFLGFLGAAGSTMGAWSQPKSKRKVC, SEQ ID NO:36); a Pep-1 (e.g., KETWWETWWTEWSQPKKKRKV (SEQ ID NO:37); a loligomer (e.g., (TPPKKKRKVEDPKKKKK)₈, SEQ ID NO:38); a pep7 and/or pep9 (e.g., SDLWEMMMVSLACQY GEAHIPTSEMREKGW, SEQ ID NO:39).

In some embodiments, a crRNA may comprise, consist essentially of, or consist of a Type-I crRNA, Type-II crRNA or Type III crRNA. In some embodiments, the Type-I crRNA, Type-II crRNA or Type III crRNA may be a processed crRNA or it may be an unprocessed crRNA, an unprocessed crRNA and a processed cRNA each comprise a 5' end and a 3' end. In representative embodiments, wherein an unprocessed Type-I crRNA, Type-II crRNA or Type III crRNA may comprise, consist essentially of, or consist of a repeat sequence having a 5' end and a 3' end, and a spacer-repeat sequence having a 5' end and a 3' end, and further wherein the repeat sequence is linked at its 3' end to the 5' end of the spacer-repeat sequence. In some embodiments, an unprocessed Type-I crRNA, Type-II crRNA or Type III crRNA (e.g., repeat-spacer-repeat) may comprise up to nine additional consecutive spacer-repeat sequences, each of the consecutive spacer-repeat sequences having a 5' end and a 3' end and each linked at its 3' end to the 5' end of the next-spacer-repeat sequence (e.g., repeat-spacer-repeat-spacer-repeat; repeat-spacer-repeat-spacer-repeat-spacer-repeat-spacer-repeat-spacer-repeat, and the like, up to 10 spacer-repeat units linked to a 5' repeat), wherein the first of the additional consecutive spacer-repeat sequences is linked at its 5' end to the 3' end of the crRNA repeat-spacer-repeat sequence.

The structure of a processed crRNA may vary between CRISPR-Cas systems. Thus, in some embodiments, a processed Type I crRNA may comprise, consist essentially of, or consist of: (A) a first portion of a Type I repeat sequence having a 5' end and a 3' end; (B) a spacer sequence having a 5' end and a 3' end; and (C) (i) a full length Type I repeat sequence having a 5' end and a 3' end, or (ii) a second portion of a Type II repeat sequence having a 5' end and a 3' end, the second portion of the Type I repeat sequence comprising: (a) a portion of consecutive nucleotides of a Type I repeat sequence from the 5'-most end of the Type I repeat sequence through the hairpin (e.g., the hairpin having a 5' end and a 3' end and the second portion comprising a portion of consecutive nucleotides of a Type I repeat sequence from the 5'-most end of the Type I repeat sequence through the 3' end of the hairpin), or (b) a portion of consecutive nucleotides of a Type I repeat sequence from the 5'-most end of the Type I repeat sequence up to the base (5' end) of the stem loop (e.g., the stem loop having a 5' end and a 3' end and the second portion comprising a portion of consecutive nucleotides of a Type I repeat sequence from the 5'-most end of the Type I repeat sequence up to the 5' end of the stem loop), wherein the spacer sequence is linked at its 5' end to the 3' end of the first portion of a Type I repeat sequence and linked at its 3' end to the 5' end of the full length Type I repeat or the 5' end of the second portion of a Type I repeat. In some embodiments, the first portion of a Type I repeat comprises from about 5 consecutive nucleotides to about 10 (e.g., 5, 6, 7, 8, 9, 10) consecutive nucleotides from the 3'-most end of the Type I repeat sequence. In representative embodiments, the first portion of a Type I repeat comprises about 8 consecutive nucleotides from the 3'-most end of the Type I repeat sequence. In some embodiments, a spacer of a Type I crRNA may be at least about 70% complementary to a target nucleic acid. In some embodiments, the spacer sequence of a Type I crRNA may comprise, consist essentially of, or consist of a length of about 25-100 nucleotides.

In some embodiments, a processed form of a Type II CRISPR-Cas system crRNA useful with this invention comprises, consists essentially of, or consists of a spacer sequence having a 5' end and a 3' end, and a Type II repeat sequence having a 5' end and a 3' end, the spacer sequence linked at the 3' end to the 5' end of the Type-II repeat sequence. In further embodiments, a Type-II crRNA may further comprise, consist essentially of or consist of a trans-activating CRISPR (tracr) sequence to form a single guide RNA (sgRNA), the single guide RNA having a 3' end and 5' end and comprising: (A) a spacer sequence having a 5' end and a 3' end, (B) a Type II repeat sequence having a 5' end and a 3' end, (C) a loop (e.g., a linker) having a 5' end and a 3' end; and (D) a trans-activating CRISPR (tracr) sequence having a 5' end and a 3' end, wherein the spacer sequence is linked at the 3' end to the 5' end of the Type II repeat sequence, the 3' end of the Type II repeat sequence is linked to the 5' end of the loop, and the 3' end of the loop is linked to the 5' end of the tracr sequence. In some embodiments, a spacer of a Type II crRNA or sgRNA is at least about 70% complementary to a target nucleic acid. Thus, in some embodiments, a sgRNA comprises a crRNA of the invention linked to a tracr via a loop or linker that can be from one nucleotide to about 100 nucleotides in length (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, and any range or value therein). In some embodiments, a spacer of a Type II crRNA may be at least about 70% complementary to a target nucleic acid. In some embodiments, the spacer sequence of a Type II crRNA and/or sgRNA may comprise, consist essentially of, or consist of a length of about 17-100 nucleotides. In some embodiments, the loop can comprise a length of one to about 100 nucleotides, wherein the 1 to about 100 nucleotides can comprise any nucleotide or nucleotide sequence.

In some embodiments, a processed form of a Type III crRNA may comprise, consist essentially of, or consist of: a first portion of a Type III repeat sequence having a 5' end and a 3' end; and a spacer sequence having a 5' end and a 3' end, wherein the spacer sequence is linked at its 5' end to the 3' end of the first portion of a Type III repeat sequence.

In some embodiments, a processed form of a Type III crRNA may comprise, consist essentially of, or consist of: (A) a first portion of a Type III repeat sequence having a 5' end and a 3' end; and (B) a spacer sequence having a 5' end and a 3' end; and (C) (i) a full length Type-III repeat sequence having a 5' end and a 3' end, or (ii) a second portion of a Type III repeat sequence having a 5' end and a 3' end, the second portion of the Type III repeat sequence comprising from about one nucleotide to about 40 consecutive nucleotides of the Type-III repeat sequence, wherein the spacer sequence is linked at its 5' end to the 3' end of the first portion of the Type III repeat sequence, and the spacer sequence is linked at its 3' end to the 5' end of the full length Type-III repeat or to the 5' end of the second portion of a Type-III repeat. In some embodiments, the first portion of a Type III repeat comprises, consists essentially of, or consists of from about 5 consecutive nucleotides to about 10 consecutive nucleotides from the 3'-most end of the Type III repeat sequence (e.g., 5, 6, 7, 8, 9, 10). In representative embodiments, the first portion of a Type III repeat comprises, consists essentially of, or consists of about 8 consecutive nucleotides from the 3'-most end of the Type III repeat sequence. In some embodiments, a spacer of a Type III crRNA may be at least about 70% complementary to a target nucleic acid. In some embodiments, the spacer sequence of a Type III crRNA may comprise, consist essentially of, or consist of a length of about 25-100 nucleotides.

In some embodiments, when linking a CPP to an unprocessed crRNA, the 5' end or the 3' end of the unprocessed crRNA may be linked to the N-terminus or the C-terminus of the CPP. In other embodiments, when linking a CPP to a processed Type I or Type III crRNA, the 3' end of the processed crRNA may be linked to the N-terminus or the C-terminus of the CPP. In representative embodiments, when linking a CPP to a processed Type II crRNA, the 5' end or the 3' end of the processed Type-II crRNA may be linked to the N-terminus or the C-terminus of the CPP. In further embodiments, when linking a CPP to sgRNA, the 5' end or the 3' end of the sgRNA may be linked to the N-terminus or the C-terminus of the CPP.

In some embodiments, a CPP-crRNA of the invention may be chemically modified to alter, for example, its transport, stability, or binding properties. Non-limiting examples of such modification include appending the side chains to the nitrogen group in the peptide backbone in the CPP (Simon et al. *Proc Natl Acad Sci USA.* 89(20):9367-71 (1992), Kolmel et al. *Eur J Med Chem.* 79:231-43 (2014)), or replacing the phosphate backbone with phosphorodiamidate, 2'-O-methyl, 2'-O-methyl 3'phosphorothioate, or 2'-O-methyl 3'thioPACE (Chui et al. *RNA* 9(9):1034-48 (2003); Hendel et al. *Nat Biotechnol.* 33(9):985-9 (2015)).

Further provided herein is an antimicrobial composition comprising, consisting essentially of, or consisting of a chimeric construct (e.g., CPP-crRNA fusion) of the invention and a carrier. In representative embodiments, a pharmaceutical composition is provided that comprises, consists essentially of, or consists of a chimeric construct of the invention in a pharmaceutically acceptable carrier.

In some embodiments, a method of killing a target cell is provided, the method comprising: contacting the target cell with an effective amount of a chimeric construct of the invention, an antimicrobial composition of the invention or a pharmaceutical composition of the invention, thereby killing the target cell. In some embodiments, a target cell can include but is not limited to a mammalian cell, a bacterial cell and/or an archaeal cell.

In some embodiments, a method of killing a target bacterial cell or a target archaeal cell is provided, the method comprising: contacting the target bacterial cell or the target archaeal cell with an effective amount of a chimeric construct of the invention, an antimicrobial composition of the invention or a pharmaceutical composition of the invention, thereby killing the target bacterial cell or the target archaeal cell. In some embodiments, the target bacterial cell can comprise an endogenous Type-I, Type-II or Type-III CRISPR-Cas system. In some embodiments, the target archaeal cell can comprise an endogenous Type-I or Type-III CRISPR-Cas system. In other embodiments, the target bacterial cell or a target archaeal cell can comprise a heterologous Type-I, Type-II or Type-III CRISPR-Cas system.

In some embodiments, the target bacterial cell or a target archaeal cell may comprise an endogenous or a heterologous Type-I CRISPR-Cas system and the target bacterial cell or target archaeal cell may be contacted with a chimeric construct comprising a Type I crRNA as described herein and/or a composition thereof. In further representative embodiments, the target bacterial cell or target archaeal cell may comprise an endogenous or a heterologous Type-II CRISPR-Cas system and the target bacterial cell or target archaeal cell may be contacted with a chimeric construct comprising a Type II crRNA and/or a composition thereof. In additional embodiments, the target bacterial cell or a target archaeal cell may comprise an endogenous or a heterologous Type-III CRISPR-Cas system and the target bacterial cell or target archaeal cell may be contacted with a chimeric construct comprising a Type IIcrRNA and/or a composition thereof.

In some embodiments, target mammalian cell may comprise a heterologous Type I, Type II or Type III CRISPR-Cas system and the target cell may be contacted with a chimeric construct comprising a Type I, Type II or Type III crRNA as described herein and/or a composition thereof.

In further embodiments, a method of treating a bacterial infection in a subject in need thereof is provided, the method comprising: administering to the subject an effective amount of a pharmaceutical composition comprising a chimeric construct of the invention in a pharmaceutically acceptable carrier, thereby treating the bacterial infection. In some embodiments, the bacterial infection may be caused by a bacterium comprising an endogenous Type-I, Type-II or Type-III CRISPR-Cas system. In some embodiments, the bacterial infection may be caused by a bacterium comprising an endogenous Type-I CRISPR-Cas system and the pharmaceutical composition that is administered may comprise a chimeric construct comprising a Type I crRNA as described herein. In further embodiments, the bacterial infection may be caused by a bacterium comprising an endogenous Type-II CRISPR-Cas system and the pharmaceutical composition that is administered may comprise a chimeric construct comprising a Type II crRNA as described herein. In additional representative embodiments, the bacterial infection may be caused by a bacterium comprising an endogenous Type-III CRISPR-Cas system and the pharmaceutical composition that is administered may comprise a chimeric construct comprising a Type III crRNA as described herein. In some embodiments of the invention, a bacterial infection may be caused by *Acinetobacter baumannii*, *Campylobacter jejuni*, *Clostridium difficile*, *Escherichia coli*, *Francisella tularensis*, *Mycobacterium tuberculosis*, *Novicida meningitidis*, *Pectobacterium atrosepticum*, *Pseudomonas aeruginosa*, *Salmonella enterica*, *Klebsiella pneumoniae*, *Staphylococcus aureus*, *Streptococcus pyogenes*, or *Streptococcus thermophilus*.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Targeted Killing of *E. coli* with Type I and Type II Systems

A.

In this example different configurations of the CPP-crRNA chimeric constructs are prepared and tested on a laboratory strain of *E. coli* equipped with different CRISPR-Cas systems. The configurations can vary in where the CPP is attached and how many CPPs are attached (FIG. 1). In some cases, the crRNA and CPP may be joined through covalent interactions, where the location of the covalent bond is varied. Both an unprocessed and processed CRISPR RNA can be tested. A fluorescent dye can be further conjugated to the complex to assess the uptake efficiency. The laboratory strain of *E. coli*, which does not express its endogenous CRISPR-Cas system under normal growth conditions (Westra et al. *Mol. Microbiol.* 77, 1380-1393 (2010)) will be equipped with a Type I-E system from *E. coli* or a Type II-A system from *Streptococcus thermophilus* based on our previous work ((Briner et al. *Mol. Cell* 56, 333-339 (2014); Gomaa et al. *mBio* 5, e00928-00913 (2014)).

Accordingly, *E. coli* with a Type I-E system (from *E. coli*) and/or at least one Type II-A system (e.g., *S. pyogenes* or *S. thermophilus*) will be targeted using the ftsA gene and one other target location and the CPP-crRNAs of the invention. The CPP-crRNAs will be tested for their ability to reduce the number of viable colonies. Defined concentrations of the CPP-crRNA fusions will be applied to bacteria in liquid culture followed by plating the culture to count the number of viable colonies. It is expected that the presence of the targeting sequence (fsA) in the spacer but not the non-targeting sequence (mviM) will substantially reduce the number of viable colonies.

Both the unprocessed and processed form of the crRNAs for the Type I-E system will be tested. The RNAs will be generated by T7 in vitro transcription. If a 5'OH is required, the RNA will be treated with a phosphatase such as calf intestinal phosphatase (CIP). The transcribed RNA will then be associated with the KFFKFFKFFK (SEQ ID NO:1) CPP using either ionic interactions or a covalent bond between the 3' end of the crRNA and the N-terminus of the CPP.

Exemplary crRNAs are provided below. Bolded portion of the sequences below designate the spacer portion of the crRNA.

```
α-ftsA CRISPR RNA
                                         (SEQ ID NO: 40)
5'OH-
AUAAACCGCUGAAGUAGAAAAACGUGUUACAGCAUCAGUUGAGUUCCCCG
CGCGAGCGGGGAU-[CPP]

α-ftsA repeat-spacer-repeat
(1)
                                         (SEQ ID NO: 41)
GAGUUCCCCGCGCGAGCGGGGAUAAACCGCUGAAGUAGAAAAACGUGUUA
CAGCAUCAGUUGAGUUCCCCGCGCGAGCGGGGAU-[CPP]

(2)
                                         (SEQ ID NO: 41)
[CPP]-GAGUUCCCCGCGCGAGCGGGGAUAAACCGCUGAAGUAGAAAAAC
GUGUUACAGCAUCAGUUGAGUUCCCCGCGCGAGCGGGGAU
```

-continued

α-mviM CRISPR RNA
(SEQ ID NO: 42)
5'OH-
AUAAACCGAGCGCGGGCAGGGUAUUCUCAUCAAACCCAUCGAGUUCCCCG
CGCGAGCGGGGAU-[CPP]

α-ftsA repeat-spacer-repeat
(1)
(SEQ ID NO: 43)
UUGAGUUCCCCGCGCGAGCGGGGAUAAACCGAGCGCGGGCAGGGUAUUCU
CAUCAAACCCAUCGAGUUCCCCGCGCGAGCGGGGAU-[CPP]

(2)
(SEQ ID NO: 43)
[CPP]-UUGAGUUCCCCGCGCGAGCGGGGAUAAACCGAGCGCGGGCAGGG
UAUUCUCAUCAAACCCAUCGAGUUCCCCGCGCGAGCGGGGAU

CPP and the crRNA are chemically synthesized the through Peptide 2.0 and Dharmacon, respectively. Dharmacon can synthesize >100-nt RNAs with 5' or 3' primary-amine modifications that allow specific cross-linking to a N-hydroxysuccinimide ester linked to the peptide's C-terminus. Both modifications come with different carbon-chain lengths, providing a tunable design parameter. A (KFF)$_3$K CPP and a crRNA targeting the ftsA gene based on our previous work (Gomaa et al. *mBio* 5, e00928-00913 (2014)) will be constructed. The efficiency of cross-linking will be determined by SDS-PAGE. The CPP and crRNA can be ordered as conjugates through Bio-Synthesis (Lewisville, Tex.).

Measure Delivery Efficiency to *E. coli*.

The crRNAs are labeled with a FITC dye and then attached to the peptide. Varying concentrations of the conjugate can then be applied to exponentially growing *E. coli* MG1655 cells in liquid culture. Flow cytometry analysis (Afroz et al. *Mol. Microbiol.* 93, 1093-1103 (2014); Afroz et al. *ACS Synth. Biol.* 4, 141-149 (2015); Luo et al. *Nucleic Acids Res.* 43, 674-681 (2015)) canl then be used to quantify the uptake of the fluorescent conjugate in individual cells. Conjugate configurations that confer fluorescence to >95% of the population when applied at <1 µM will be selected.

Assess targeted killing of *E. coli*. The best conjugates from the above study will be tested for targeted killing of *E. coli* MG1655 strain equipped with the Type I-E system from *E. coli* or a Type H-A system from *S. thermophilus*. Plasmids constitutively expressing the requisite genes (6 cas genes for the Type I-E system, 1 cas gene and 1 tracrRNA for the II-A system), which have used in previous work (Gomaa et al. *mBio* 5, e00928-00913 (2014); Briner et al. *Mol. Cell* 56, 333-339 (2014)) will be used. Conjugates will then be applied to exponentially growing cells, followed by tracking cell viability based on turbidity and colony-forming units. Conjugate configurations that elicit >99.9% reduction in bacterial titers when the CPP-CRISPR RNA conjugate is applied at <1 µM will be selected.

Measure Uptake of Conjugates in Each Representative Species.

Evaluation of the ability of the best-performing conjugates to enter the strains representing the different commercialization routes will be evaluated. The original (KFF)$_3$K CPP and at least one other CPP previously validated in that type of bacteria (e.g., (RXR)$_4$B for *S. aureus*) will be undertaken. Uptake will be assessed by flow cytometry analysis. The CPP that best allows uptake of the CRISPR RNA when applied at <1 µM into at least one of the representative strains will be selected.

Assess Targeted Killing of Representative Species.

We will follow similar approaches as laid out for targeted killing of *E. coli*. The major difference will be redesigning the CRISPR RNAs to operate through the endogenous CRISPR-Cas system of each representative strain. The crRNA is designed with a spacer targeting a site in the genome along with the flanking repeat. In Type I and Type II CRISPR-Cas systems, the protospacer-adjacent motif required for targeting will need to be identified (Mojica et al. *Microbiol. Read. Engl.* 155, 733-740 (2009)). The designed conjugates will be applied to each bacterium following the same procedure laid for *E. coli*.

B. Type I-E

*E. coli* strains BW25113+cas and BW25113Δcas were grown in LB media to mid-log phage (OD$_{600}$=about 0.5) and then diluted in LB to OD$_{600}$=0.0001 (about $10^5$ cfu/ml). BW25113 Δcas3 expresses the I-E Cascade genes (casA-BCDE) from the genome under the control of a constitutive promoter (Luo et al. Nucleic Acids Res. 43, 674-681 (2015)). BW25113+cas similarly expresses the I-E Cascade genes from the genome and the I-E cas3 gene under the control of a constitutive promoter on a plasmid. Under this setup, an introduced crRNA would guide Cascade to bind target sequences and recruit Cas3 to cleave and degrade the target. Cascade alone can repress gene repression (Luo et al. Nucleic Acids Res. 43, 674-681 (2015)), which could be lethal when targeting an essential gene.

Lyophilized treatments [CPP (cell-penetrating peptide), CPP-crRNA conjugate, and crRNA] were resuspended in nuclease-free water to a concentration of 10 µM. Using the 10 µM, 1 µM and 0.1 µM aliquots of each treatment were made. Each treatment would be applied to *E. coli* at one of 3 final concentrations (1 µM, 0.1 µM, and 0.01 µM), resulting in a total of 9 different treatment conditions for each *E. coli* strain.

The crRNA in these experiments was a Type I-E [partial repeat]-[spacer]-[repeat] sequence targeting the *E. coli* ftsA gene (sequence: 5'-AUA AAC CGC UGA AGU AGA AAA ACG UGU UAC AGC AUC AGU UGA GUU CCC CGC GCG AGC GGG GAU-3') (SEQ ID NO:40). The CPP peptide sequence was: KFFKFFKFFK (SEQ ID NO:1). The linker joining the CPP to the crRNA in the conjugate was: C6 amino-SMCC-Cys.

In a first 96-well plate, 180 µl of 1) OD$_{600}$=0.0001 *E. coli* BW25113+cas, 2) OD$_{600}$=0.0001 *E. coli* BW25113Δcas, or 3) LB media (blank control) was added to each well. 20 µl of treatment (CPP, CPP-crRNA conjugate, or crRNA, at concentrations of 1 µM, 0.1 µM, of 0.01 µM) was then added to each well of *E. coli*. 20 µl µl water was added to each well of LB media as a control. 100 µl from each well was then transferred to a second 96-well plate.

The first plate was incubated in a 96-well plate reader shaking at 37° C. over 12 hrs with an OD$_{630}$ measurement taken every 15 min. The second plate was incubated for 35 min at 37° C. and shaking at 250 rpm before 10 µl from each well was transferred to a new plate for early evaluation of colony-forming units (CFUs). Incubation of this plate then resumed for another 1 hr and 25 min, at which point a second evaluation of CFUs was conducted.

Figure 2A:
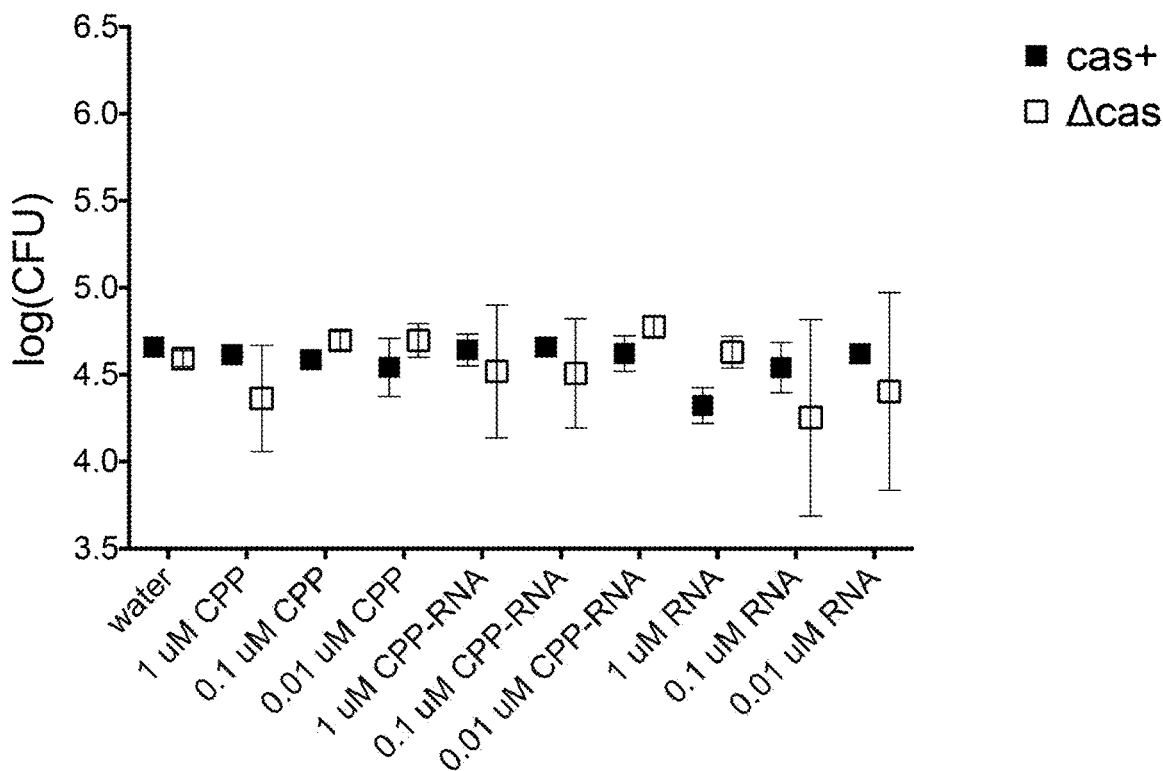
Figure 2B:
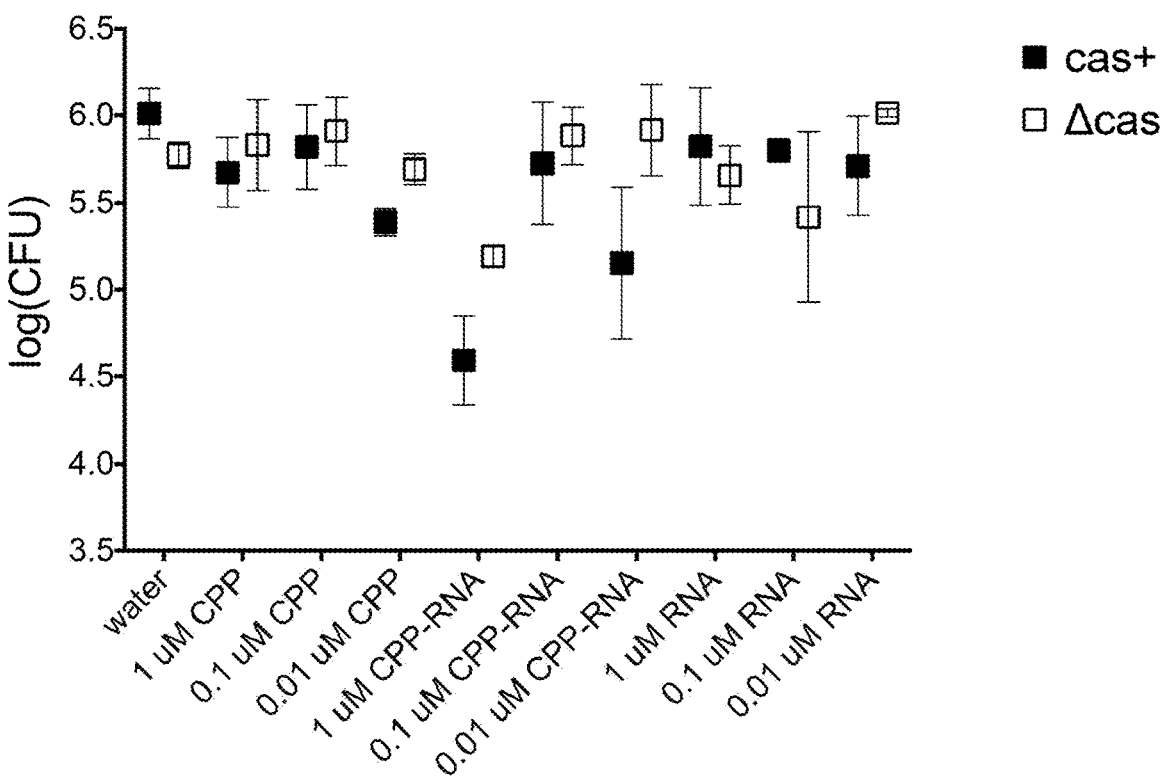

The results show effectiveness, as measured by CFU count, of the CPP-crRNA conjugate at a concentration of 1 µM after 2 hours of treatment (FIG. 2B), with increased killing in the BW25113+cas strain. No effect was observed after 35 minutes of treatment (FIG. 2A).

Similarly, the results show effectiveness, as measured by optical density at 630 nm (increase in time to reach mid-log growth phage), of the CPP-crRNA conjugate at a concentration of 1 µM, with increased effectiveness in the BW25113+cas strain (FIG. 2C). The CPP-crRNA conjugates were also somewhat effective in the strain expressing only Cascade, which is expected given that ftsA is an essential gene and its repression would be expected to be lethal.

C. Type I-E

*E. coli* strains 8739 (has Type I-E CRISPR) and 25922 (does not have Type I-E CRISPR) were grown in LB media to mid-log phage ($OD_{600}$=about 0.5) and then diluted in LB to $OD_{600}$=-0.0001 (about $10^5$ cfu/ml).

Lyophilized treatments [CPP (cell-penetrating peptide), CPP-crRNA conjugate, and crRNA] were resuspended in nuclease-free water to a concentration of 10 μM.

The crRNA in these experiments was a Type I-E [partial repeat]-[spacer]-[repeat] sequence targeting the *E. coli* ftsA gene (sequence: 5'-AUA AAC CGC UGA AGU AGA AAA ACG UGU UAC AGC AUC AGU UGA GUU CCC CGC GCG AGC GGG GAU-3') (SEQ ID NO:40). The CPP peptide sequence was: KFFKFFKFFK (SEQ ID NO:1). The linker joining the CPP to the crRNA in the conjugate was: C6 amino-SMCC-Cys.

In a first 96-well plate, 180 μl of 1) $OD_{600}$=0.0001 *E. coli* 8739, 2) $OD_{600}$=0.0001 *E. coli* 25922, or 3) LB media (blank control) was added to each well. 20 μl of treatment (CPP, CPP-crRNA conjugate, or crRNA) was then added to each well of *E. coli* to yield final concentrations of 1 μM. 20 μl water was added to each well of LB media as a control. 1000 from each well was then transferred to a second 96-well plate.

The first plate was incubated in a 96-well plate reader shaking at 37° C. over 12 hrs with an $OD_{630}$ measurement taken every 15 min. The second plate was incubated for 2 hours at 37° C. shaking at 250 rpm, at which point an evaluation of colony-forming units (CFUs) was conducted.

Figure 3A:
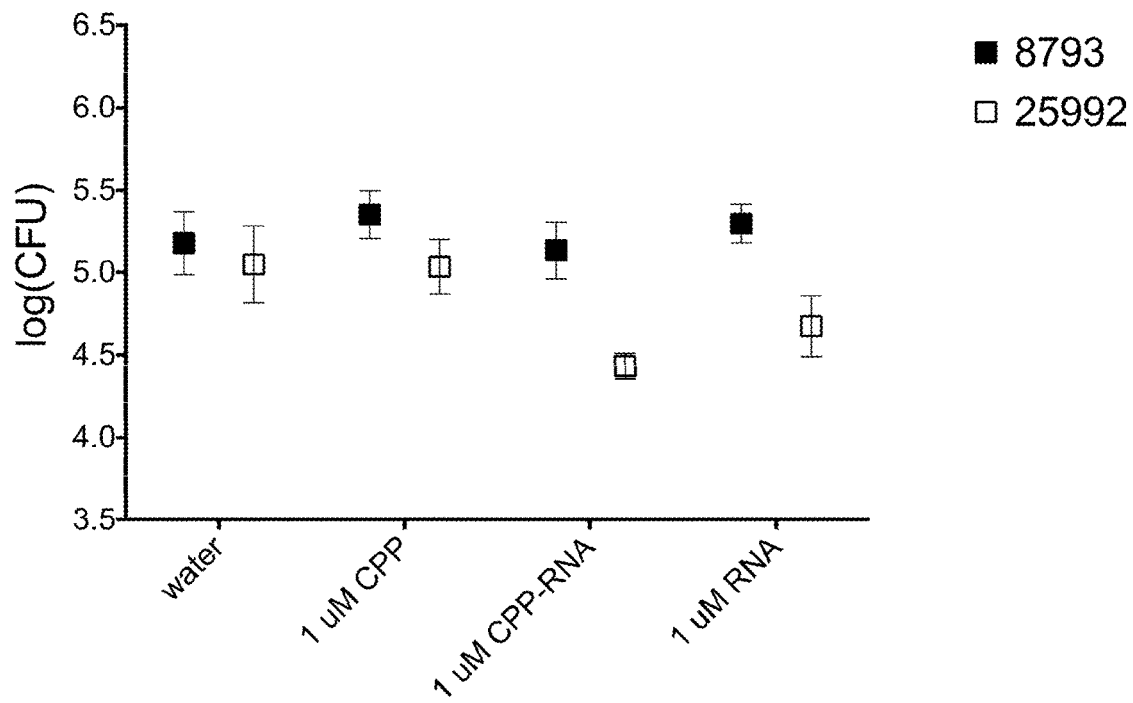
FIGS. 3A-3B show that delivery of Type I-E CRISPR RNAs using CPPs elicits cell death in treated wild-type strains of *E. coli*.
Figure 3B:
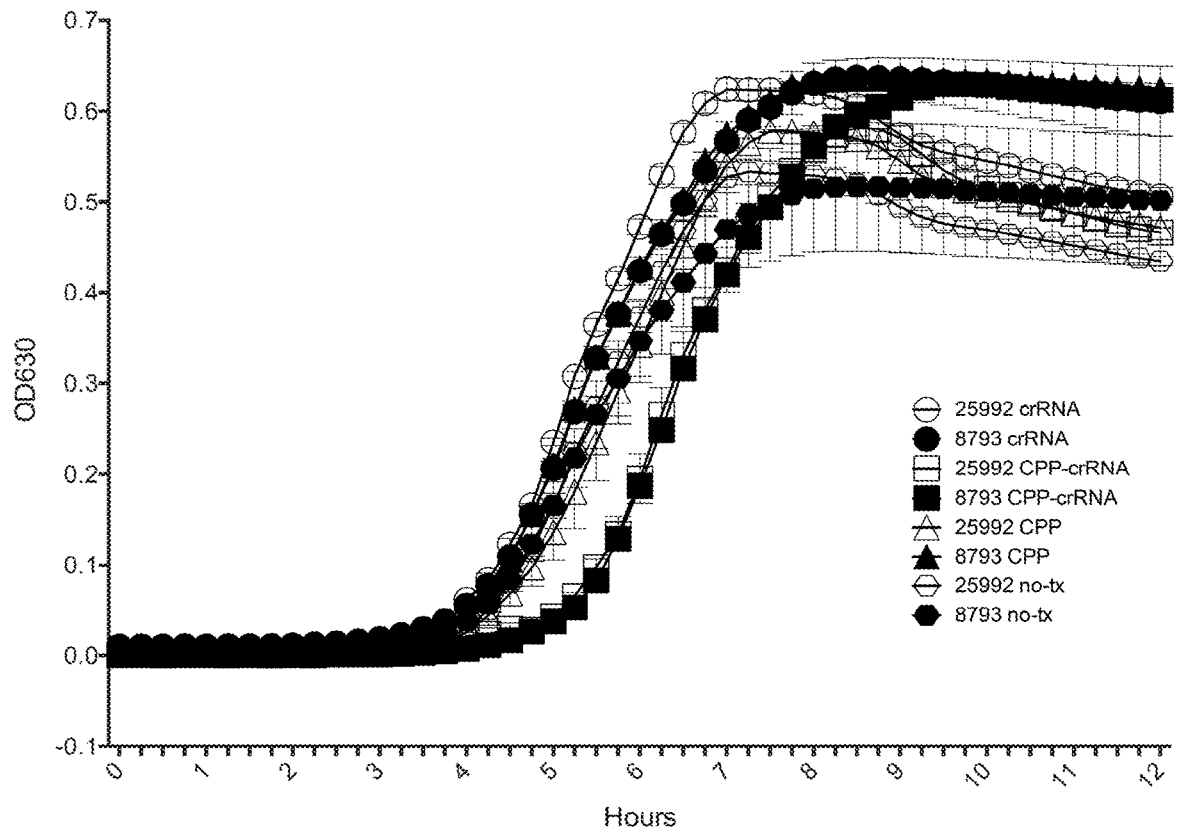

The results showed no effect of the CPP-crRNA conjugate as measured by CFU count (FIG. 3A). In contrast, a small effect of the CPP-crRNA conjugate in both strains of *E. coli* was detected as measured by optical density at 630 nm (increase in time to reach mid-log growth phage) (FIG. 3B). These limited effects likely reflect the absence of an actively expressed CRISPR-Cas system in both strains.

D. Type II-A

*E. coli* pCas9 (encodes genes for Cas9 and for the tracrRNA) and *E. coli* pBAD33 (plasmid backbone for pCas9) were grown in LB media to mid-log phage ($OD_{600}$=about 0.5) and then diluted in LB to $OD_{600}$=0.0001 (about $10^5$ cfu/ml).

Lyophilized treatments [CPP (cell-penetrating peptide), CPP-crRNA conjugate, and crRNA] were resuspended in nuclease-free water to a concentration of 10 μM.

The crRNA in these experiments was a Type II-A [spacer]-[repeat] sequence targeting the *E. coli* zraP gene (sequence: 5'-UAA CGC GGU CGC CAA AGA GAG UUU UAG AGC UGU GCU GUU UUG AAU GGU CCC AAA AC-3') (SEQ ID NO:44). The CPP peptide sequence was: KFFKFFKFFK (SEQ ID NO:1). The linker joining the CPP to the crRNA in the conjugate was: C6 amino-SMCC-Cys.

In a first 96-well plate, 180 μl of 1) $OD_{600}$=0.0001 *E. coli* pCas9, 2) $OD_{600}$=0.0001 *E. coli* pBAD33, or 3) LB media (blank control) was added to each well. Twenty microliters of treatment (CPP, CPP-crRNA conjugate, or crRNA) was then added to each well of *E. coli* to yield final concentrations of Twenty microliters of water was added to each well of LB media as a control. One hundred microliters from each well was then transferred to a second 96-well plate.

The first plate was incubated in a 96-well plate reader shaking at 37° C. over 12 hrs with an $OD_{630}$ measurement taken every 15 min. The second plate was incubated for 2 hours at 37° C. shaking at 250 rpm, at which point an evaluation of colony-forming units (CFUs) was conducted.

Figure 4A:
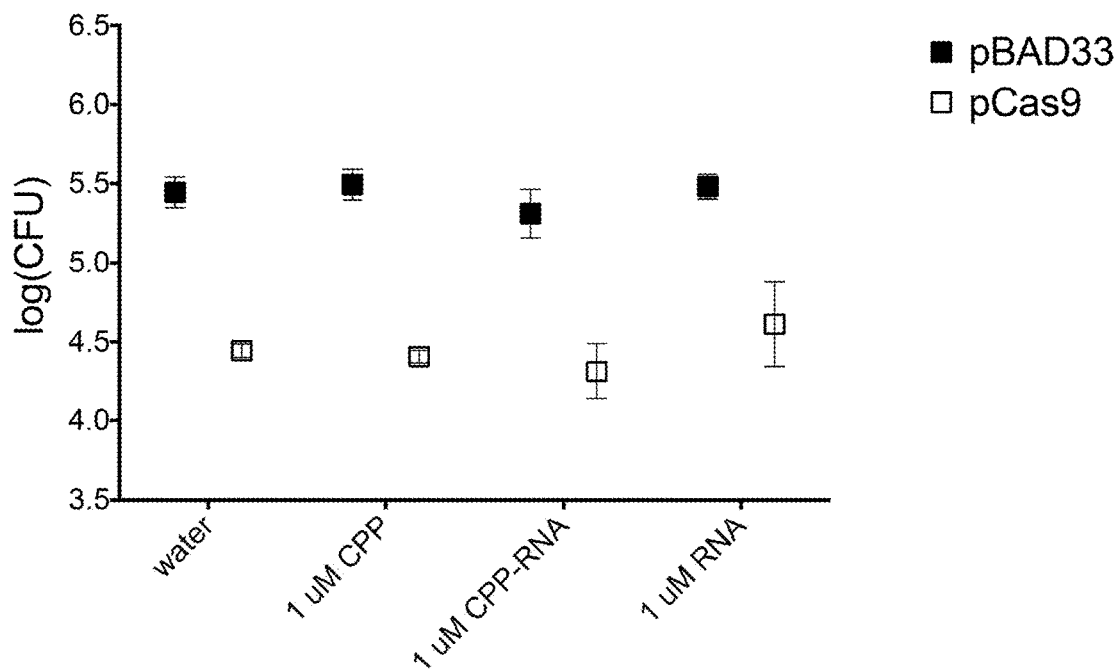
FIG. 4A shows the effect of the different Type II CRISPR RNA treatments as measured by cfu and FIG. 4B shows the effect of the different treatments as measured by optical density at 630 nm.
Figure 4B:
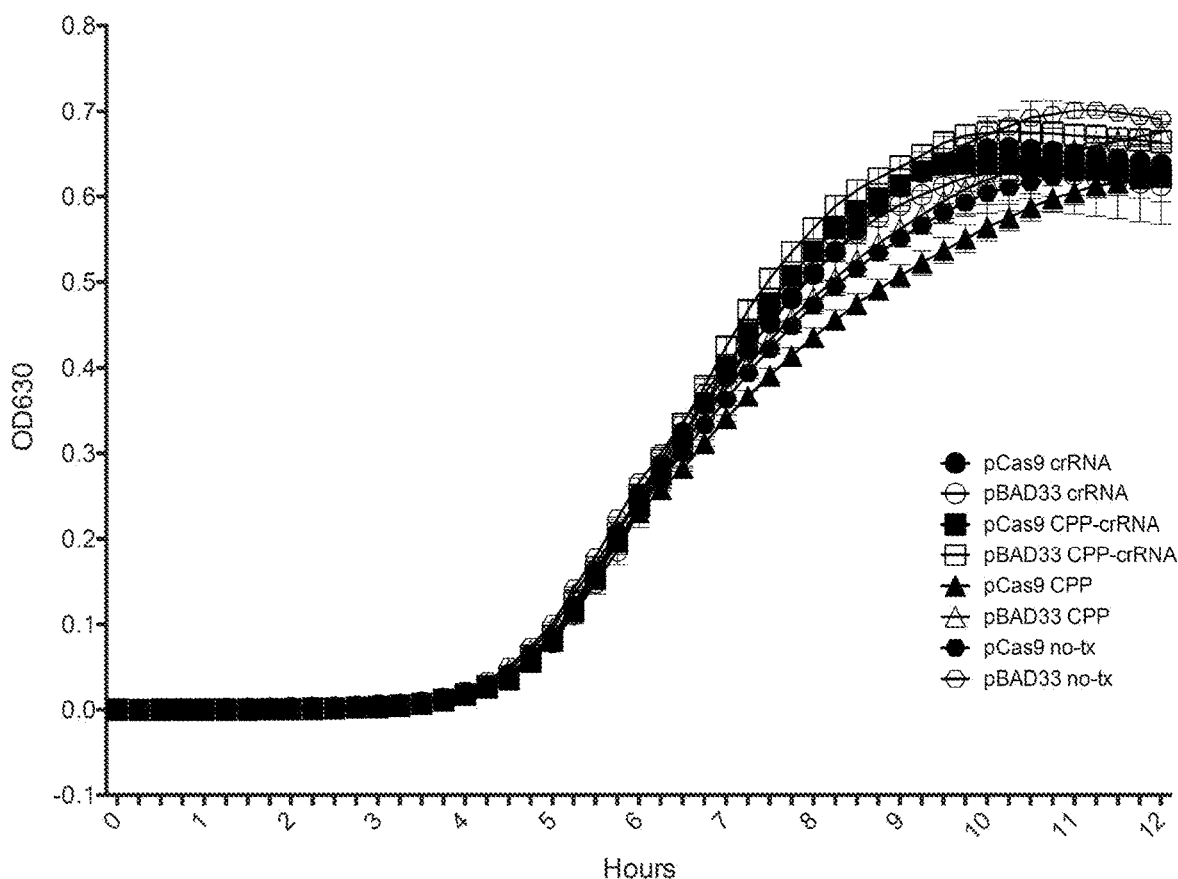

The results showed no effect of the CPP-crRNA conjugate as measured by CFU count (FIG. 4A) and by optical density at 630 nm (FIG. 4B). This may be due to the limited lethality of Cas9 in *E. coli* (Cui & Bikard, *Nucleic Acids Res.*, 44, 4243-4251 (2016)).

Example 2. Targeted Killing of *Streptococcus thermophilus*

Intracellular delivery and targeted killing in strains of commercial relevance are evaluated using configurations developed in Example 1. Such commercially relevant bacteria include *Clostridium difficile* (human therapeutics), *Salmonella enterica* (food safety), and *Streptococcus thermophilus* (industrial contaminant) crRNAs are designed to target sequences distinct to each bacterium and CRISPR-Cas system, providing an unparalleled level of specificity. Testing the CPP-CRISPR RNA conjugates will reveal which species are most susceptible to this antimicrobial strategy, offering guidance on the content of a provisional patent application.

*S. thermophilus* LMD-9 encodes three different endogenous CRISPR-Cas systems (two orthogonal type II-A's, and a type III) where the two Type II-A systems have been shown to be active under normal growth conditions. crRNAs will be designed to be compatible with either Type II system and target different locations in the genome. An exemplary crRNA for testing includes a 20 nucleotide spacer sequence linked to a full length repeat sequence. Liquid cultures of *S. thermophilus* will be contacted with different concentrations of the CPP-crRNAs, dilutions of the cells will be plates, and the number of colonies counted. The number of colonies is expected to be greatly reduced when the cultures are contacted with sub-micromolar concentrations of the genome-targeting crRNA, and no difference is expected to be observed between untreated cells and cells contacted with a non-targeting crRNA (comprising a spacer comprising a target DNA) or a genome-targeting crRNA lacking a CPP.

Exemplary crRNAs are provided below. Bolded portion of the sequences below designate the spacer portion of the crRNA.

α-dnaE CRISPR RNA (Sth1)
(SEQ ID NO: 45)
AUCAGCUCCUUUUCUCGGCCGUUUUUGUACUCUCAAGAUUUAAGUAACUG
UACAAC-[CPP]

α-mviM CRISPR RNA (Sth1) (non-targeting control)
(SEQ ID NO: 46)
GUAUUCUCAUCAAACCCAUCGUUUUUGUACUCUCAAGAUUUAAGUAACUG
UACAAC-[CPP]

α-dnaE CRISPR RNA (Sth3)
(SEQ ID NO: 47)
ACAACCUCUCUCAACCGUCCGUUUUGGAACCAUUCGAAACAACACAGCUC
UAAAAC-[CPP]

α-mviM CRISPR RNA (Sth3) (non-targeting control)
(SEQ ID NO: 48)
GUAUUCUCAUCAAACCCAUCGUUUUGGAACCAUUCGAAACAACACAGCUC
UAAAAC-[CPP]

Example 3. Plasmid Removal in *Staphylococcus epidermidis*

The use of endogenous Type III CRISPR-Cas systems and the chimeric constructs of the invention for plasmid removal is evaluated in the human commensal bacterium *Staphylococcus epidermidis*. This bacterium naturally possesses an endogenous CRISPR-Cas system that was previously shown to target DNA (Marraffini and Sontheimer *Science* 322 (5909): 1843-1845 (2008)). The bacterium harboring the pG0400 conjugation plasmid will be grown under non-selective conditions in liquid culture and contacted with CPP-crRNA fusions designed to target defined sites in the conjugation plasmid. The culture will then be plated on solid medium with or without mupirocin selection, and the ratio of colonies under selective and non-selective plating conditions will be determined. The expectation is that the presence of a plasmid-targeting crRNA will greatly reduce the number of colonies under selective conditions by directing the removal of the plasmid. This will be further confirmed by performing qRT-PCR against a region of the plasmid in cultures that were untreated, treated with a non-targeting CPP-crRNA, or a targeting CPP-crRNA.

Exemplary crRNAs are provided below. Bolded portion of the sequences below designate the spacer portion of the crRNA.

α-pGO CRISPR RNA
(1)
(SEQ ID NO: 49)
ACGAGAACACGUAUGCCGAAGUAUAUAAAUCAUCAGUACAAAGGAT-[CPP]

(2)
(SEQ ID NO: 50)
GAUCGAUACCCACCCCGAAGAAAAGGGGACGAGAACACGUAUGCCGAAGU AUAUAAAUCAUCAGUACAAAGGAUCGAUACCCACCCCGAAGAAAAGGGGA CGAGAAC-[CPP]

α-mviM CRISPR RNA (non-targeting control)
(1)
(SEQ ID NO: 51)
ACGAGAACAGCGCGGGCAGGGUAUUCUCAUCAAACCCAUCAGAGAT-[CPP]

(2)
(SEQ ID NO: 52)
GAUCGAUACCCACCCCGAAGAAAAGGGGACGAGAACAGCGCGGGCAGGGU AUUCUCAUCAAACCCAUCAGAGAUCGAUACCCACCCCGAAGAAAAGGGGA CGAGAAC-[CPP]

The foregoing is illustrative of the present invention, and is not to be construed as limiting thereof. The invention is defined by the following claims, with equivalents of the claims to be included therein.

That which is claimed is:

1. A method of killing a target bacterial cell comprising contacting the target bacterial cell with a pharmaceutical composition comprising
   (a) a cell penetrating peptide (CPP) complexed with a CRISPR RNA (crRNA); and
   (b) a pharmaceutically acceptable excipient,
      wherein the crRNA is a processed Type I crRNA comprising a repeat-spacer having about eight consecutive nucleotides of a Type I repeat sequence and a spacer sequence having a length of about 32 nucleotides, a processed Type II crRNA comprising a spacer-repeat having spacer sequence with a length of about 20 nucleotides and about 20 consecutive nucleotides of a Type II repeat sequence, or a processed Type III crRNA comprising a repeat-spacer having about eight consecutive nucleotides of a Type III repeat sequence and a spacer sequence having a length of about 32 nucleotides;
      wherein the processed Type II crRNA does not further comprise a trans-activating CRISPR (tracr) sequence;
      wherein the spacer sequence of the Type I crRNA, the Type II crRNA, and the Type III crRNA is complementary to a target sequence in the target bacterial cell, the target bacterial cell comprises a CRISPR-Cas system, and the crRNA is operable with the CRISPR-Cas system, thereby killing the target bacterial cell.

2. The method of claim 1, wherein the CRISPR-Cas system comprises a Type I CRISPR-Cas system that is operable with the processed Type I crRNA, a Type II CRISPR-Cas system that is operable with the processed Type II crRNA, or a Type III CRISPR-Cas system that is operable with the processed Type III crRNA.

3. The method of claim 2, wherein the target bacterial cell comprises the Type I CRISPR-Cas system.

4. The method of claim 3, wherein the Type I CRISPR-Cas system comprises Cascade polypeptides that are operable with the processed Type I crRNA.

5. The method of claim 4, wherein the target bacterial cell comprises a Cas3.

6. The method of claim 1, wherein the bacterial cell is *Acinetobacter baumannii, Campylobacter jejuni,*

*Clostridium difficile, Escherichia coli, Francisella tularensis, Mycobacterium tuberculosis, Novicida meningitidis, Pectobacterium atrosepticum, Pseudomonas aeruginosa, Salmonella enterica, Klebsiella pneumoniae, Staphylococcus aureus, Streptococcus pyogenes*, or *Streptococcus thermophilus*.

7. The method of claim 1, wherein the bacterial cell is a bacterial pathogen.

8. The method of claim 1, wherein the CPP is complexed with the crRNA via a linker.

* * * * *

UNITED STATES PATENT AND TRADEMARK OFFICE
CERTIFICATE OF CORRECTION

PATENT NO. : 11,286,480 B2
APPLICATION NO. : 15/762730
DATED : March 29, 2022
INVENTOR(S) : Beisel et al.

It is certified that error appears in the above-identified patent and that said Letters Patent is hereby corrected as shown below:

In the Specification

Column 38, Line 36: Please correct "(fsA)" to read -- (ftsA) --

Column 41, Line 8: Please correct "-0.0001" to read -- 0.0001 --

Column 41, Line 27: Please correct "1000" to read -- 100 µL --

Signed and Sealed this
Thirtieth Day of August, 2022

Katherine Kelly Vidal
*Director of the United States Patent and Trademark Office*